(12) United States Patent
Baptiste et al.

(10) Patent No.: US 11,123,272 B2
(45) Date of Patent: Sep. 21, 2021

(54) COSMETIC BLENDS

(71) Applicant: Symrise AG, Holzminden (DE)

(72) Inventors: Caroline Baptiste, Paris (FR); Aurélie Trunet, Paris (FR); Gabriele Vielhaber, Colombes (FR); Sabine Lange, Holzminden (DE); Dominik Stuhlmann, Holzminden (DE); Benoit Join, Holzminden (DE); Oskar Koch, Göttingen (DE)

(73) Assignee: Symrise AG, Holzminden (DE)

( * ) Notice: Subject to any disclaimer, the term of this patent is extended or adjusted under 35 U.S.C. 154(b) by 0 days.

(21) Appl. No.: 16/465,228

(22) PCT Filed: Dec. 2, 2016

(86) PCT No.: PCT/EP2016/079591
§ 371 (c)(1),
(2) Date: May 30, 2019

(87) PCT Pub. No.: WO2018/099570
PCT Pub. Date: Jun. 7, 2018

(65) Prior Publication Data
US 2020/0121575 A1     Apr. 23, 2020

(51) Int. Cl.
*A61K 8/34* (2006.01)
*A61Q 19/00* (2006.01)
*A61Q 19/10* (2006.01)
*A61Q 15/00* (2006.01)
*A61Q 5/02* (2006.01)
*A61Q 19/08* (2006.01)
*A61Q 17/04* (2006.01)
*A61Q 11/00* (2006.01)

(52) U.S. Cl.
CPC .............. *A61K 8/347* (2013.01); *A61K 8/345* (2013.01); *A61Q 5/02* (2013.01); *A61Q 11/00* (2013.01); *A61Q 15/00* (2013.01); *A61Q 17/04* (2013.01); *A61Q 19/00* (2013.01); *A61Q 19/002* (2013.01); *A61Q 19/007* (2013.01); *A61Q 19/08* (2013.01); *A61Q 19/10* (2013.01)

(58) Field of Classification Search
None
See application file for complete search history.

(56) References Cited

U.S. PATENT DOCUMENTS

| | | | | |
|---|---|---|---|---|
| 5,895,657 | A * | 4/1999 | Fournet | A21D 2/14 424/401 |
| 7,166,435 | B2 * | 1/2007 | Rosenbloom | A61K 9/006 435/6.14 |
| 7,582,681 | B2 * | 9/2009 | Schmaus | A01N 31/02 514/738 |
| 2006/0269500 | A1 | 11/2006 | Riemer et al. | |
| 2007/0148103 | A1 | 6/2007 | Harvey | |
| 2008/0014162 | A1 * | 1/2008 | Willemin | A61Q 17/00 424/70.1 |
| 2009/0054520 | A1 | 2/2009 | Surburg et al. | |
| 2009/0269290 | A1 | 10/2009 | Patnode | |
| 2013/0129646 | A1 | 5/2013 | Vielhaber et al. | |
| 2013/0210921 | A1 * | 8/2013 | Hirayama | A61K 8/375 514/627 |
| 2014/0113971 | A1 | 4/2014 | Zhang et al. | |
| 2016/0206523 | A1 | 7/2016 | Obias et al. | |

FOREIGN PATENT DOCUMENTS

| | | | |
|---|---|---|---|
| CN | 105 853 278 A | 8/2016 | |
| DE | 10 2006 060439 A1 | 6/2008 | |
| KR | 2013-0088665 A | 8/2013 | |
| WO | WO-2009087578 A2 * | 7/2009 | ............. A61K 8/046 |

OTHER PUBLICATIONS

P. Sricharoen, et al. Phytochemicals in Capsicum oleoresin, Ultrasonics Sonochem. 38 (2017) 629-639). (Year: 2017).*
Database GNPD [Online] Mintel; Sep. 1, 2015 (Sep. 1, 2015) 9 "Neck & Shoulder Muscle Relax Balm," XP002766269, Database accession No. 3401677, Product Description Ingredients.
Database GNPD [Online] Mintel; Jul. 1, 2014 (Jul. 1, 2014) , "Soya Blackhead Heating Mask," XP002766270 , Database accession No. 2568073 Product description Ingredients.

* cited by examiner

*Primary Examiner* — Michael P Cohen
(74) *Attorney, Agent, or Firm* — Dilworth & Barrese, LLP

(57) ABSTRACT

Suggested is a cosmetic blend, comprising or consisting of (a) at least one TRPV1 and/or TRPV3 modulator and (b1) at least one 1,2-alkandiol having 5 to 12 carbon atoms and/or (b2) at least one polyol having 3 to 12 carbon atoms and 3 to 6 hydroxyl groups.

10 Claims, 2 Drawing Sheets

COSMETIC BLENDS

FIELD OF INVENTION

Figure 1:
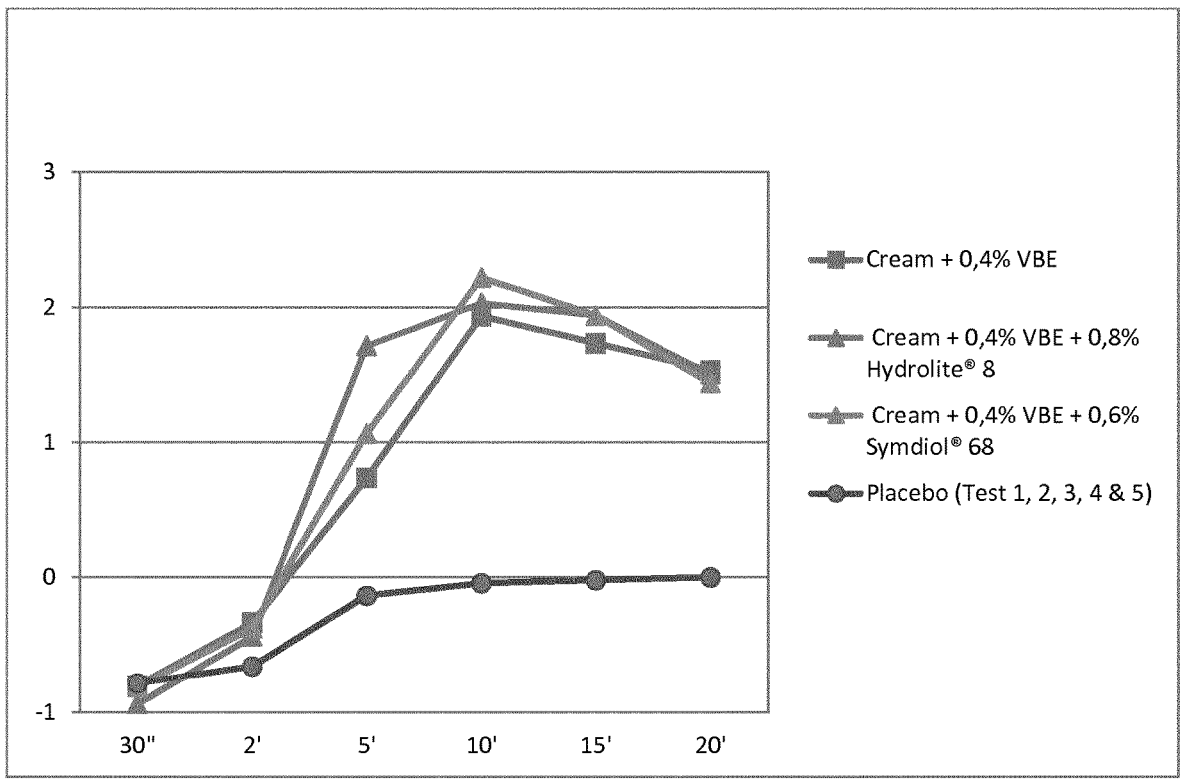

The present invention belongs to the area of cosmetics and refers to new mixtures comprising warming agents with reduced negative side effects, compositions comprising said mixtures, a method for improving warming sensation on human skin or mucous membranes, and the use of specific hydroxyl compounds as performance boosters for warming agents.

STATE OF THE ART

The transient receptor potential cation channel subfamily V member 1 (TRPV1) or member 3 (TRPV3), also known as the capsaicin receptor and the vanilloid receptor 1 or 3, are proteins that, in humans, are encoded by the TRPV1 or TRPV3 gene. TrpV1 was the first isolated member of the transient receptor potential vanilloid receptor proteins that in turn are a sub-family of the transient receptor potential protein group. The function of TRPV1 is detection and regulation of body temperature. In addition, TRPV1 is involved in the sensation of scalding heat and pain (nociception).

TRPV1/3 is a nonselective cation channel that may be activated by a wide variety of exogenous and endogenous physical and chemical stimuli. The best-known activators of TRPV1 are:

a temperature above 43° C.;
acidic conditions;
capsaicin (the irritating compound in hot chili peppers); and
allyl isothiocyanate (the pungent compound in mustard and wasabi)i.

More than TRPV1 TRPV3 leads to a painful, burning sensation. Its endogenous activators include: low pH (acidic conditions), the endocannabinoid anandamide, N-oleyl-dopamine, and N-arachidonoyl-dopamine. TRPV1/3 receptors are found mainly in the nociceptive neurons of the peripheral nervous system, but they have also been described in many other tissues, including the central nervous system and the skin. TRPV1/3 is involved in the transmission and modulation of pain (nociception), as well as the integration of diverse painful stimuli.

Agonists such as capsaicin and resiniferatoxin activate TRPV1/3 and, upon prolonged application, cause TRPV1 activity to decrease (desensitization), leading to alleviation of pain via the subsequent decrease in the TRPV1/3 mediated release of pro-inflammatory molecules following exposures to noxious stimuli. Agonists can be applied locally to the painful area in various forms, generally as a patch or an ointment. Numerous capsaicin-containing creams are available over the counter, containing low concentrations of capsaicin (0.025-0.075%). It is debated whether these preparations actually lead to TRPV1/3 desensitization; it is possible that they act via counter-irritation.

TRPV1 modulators or agonists have been described in, for example, WO 2007 054480 A1 (MERCK), which teaches the effect of 2-(benzimidazol-1-yl)-acetamide derivatives in the treatment of TRPV1 related diseases.

WO 2008 079683 A1 (ABBVIE) teaches compounds being a conjugated two ring system of cyclohexyl and phenyl for inhibiting TRPV1 receptor.

EP 01939173 A1 (SERENTRIX) discloses O-substituted-dibenzyl urea- or thiourea-derivatives as TRPV1 receptor antagonists.

WO 2008 076752 A1 (JANSSEN) teaches benzoimidazole compounds as potent TRPV1 modulators.

EP 01908753 A1 (MOCHIDA) is related to TRPVI modulators being heterocyclidene acetamide derivatives.

Finally, EP 2700431 A1 (ANALYTICON) refers to specific plant extracts for the same purpose.

Agents capable of modulating TRPV1/3 activity (also called TRPV agonists) like for example capsaicin or certain vanillyl compounds are frequently used in cosmetic and oral compositions, since they provide a specific warming sensation when applied to human skin or mucous membranes. Unfortunately, the warming sensation is typically accompanied by unwanted side effects, like irritation, inflammation, burning, itching, redness, pain and the like. These effects limit the concentration one can add TRPV1/3 modulators to cosmetic formulations, and of course limit the desired warming effect too.

Therefore, the problem underlying the present invention has been improving ("boosting") the warming sensation provided by TRPV1/TRPV3 modulators on human skin or mucous membranes, while at the same time reducing negative side effects.

DESCRIPTION OF THE INVENTION

Object of the present invention is a cosmetic blend, comprising or consisting of
(a) at least one TRPV1 and/or TRPV3 modulator and
(b1) at least one 1,2-alkandiol having 5 to 12 carbon atoms and/or
(b2) at least one polyol having 3 to 12 carbon atoms and 3 to 6 hydroxyl groups.

Surprisingly, it has been observed that adding said specific hydroxyl compounds, in particular 1,2-alkandiol to said TRPV1 and/or TRPV3 modulators, particularly to vanillyl ethers, simultaneously increases warming sensation on human skin or mucous membranes, while unwanted side effects of the modulators, namely various types of skin irritation (e.g. burning, itching, redness, stinging, pain) is significantly reduced. This is especially surprising, since a simple penetration enhancement effect caused by the alkandiols would also lead to increasing side effects.

Therefore, the invention provides a teaching how to achieve the same level of warming sensation by using lower amounts of TRPV1/TRPV3 modulators while simultaneously improving dermatological compatibility of modulators, either in a blend or a customer formulation. It is also possible to increase warming sensation by adding the hydroxyl compounds to a given concentration of TRPV1/TRPV3 modulators, while at the same time the negative side effects on skin are decreased.

TRPV1/TRPV3 Modulators

It should be noted that the terms "modulator" and "agonist" with regard to substances influencing the activity of TRPV1 and TRPV3 are used in the same manner. According to the present invention the TRPV1 and/or TRPV3 modulators are selected from the group consisting of:

vanillyl derivatives, preferably vanillyl ethers,
capsaicin,
allyl isothiocyanate;
gingerol,
4-(1-menthoxymethyl)-2-phenyl-1,3-dioxolan,
4-(1-menthoxymethyl)-2-(3',4'-dihydroxyphenyl)-1,3-dioxolan,
4-(1-menthoxymethyl)-2-(2'-hydroxy-3'-methoxyphenyl)-3-dioxolan, 4-(1-menthoxymethyl)-2-(4'-methoxyphenyl)-3-dioxo-
  lan,
4-(1-menthoxymethyl)-2-(3',4'methylenedioxyphenyl)-3-
  dioxolan,
4-(1-menthoxymethyl)-2-(3'-methoxy-4'-hydroxyphe-
  nyl)-3-dioxolan,
red pepper oil,
red pepper oleoresin,
ginger oleoresin,
nonylic acid vanillyl amide,
jambu oleoresin,
*Zanthoxylum piperitum* extract,
sanshool I,
sanshool II,
sanshoamide,
black pepper extract,
chavicine,
piperine,
spilanthol, and
the modulators or warming agents disclosed in U.S. Pat.
  No. 6,780,443 (as far as the nature of the modulators
  are concerned this document is hereby incorporated by
  reference) and their mixtures In a preferred embodiment said TRPV1 and/or TRPV3 modulators represent a vanillyl ether according to formula (I)

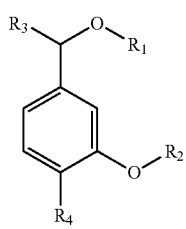

(I)

wherein
R1 stands for hydrogen, or a C1-C7 alkyl group;
R2 stands for a C1-C3 alkyl radical,
R3 stands for hydrogen or a C3-C9 alkoxyl group;
R4 stands for hydroxyl or a OC(O)CH3 group; and
wherein R2 and R3 can be covalent bounded to form a cyclic acetal;
said acetal optionally substituted by a C2-C8 alkyl group.

In a particularly preferred embodiment said TRPV1 and/or TRPV3 modulators represent a vanillyl ether according to formula (II)

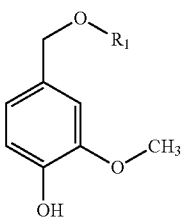

(II)

wherein R1 stand for hydrogen or a C1-C7 alkyl group.
Most preferred said TRPV1 and/or TRPV3 modulator represents a vanillyl ether according to formula (III)

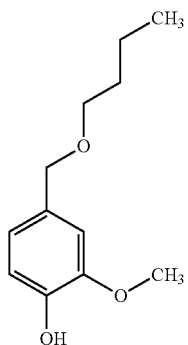

(III = Vanillyl butyl ether VEB)

Hydroxyl Compounds

A first group of species forming group (b1) and acting as "boosters" for the TRPV1/TRPV3 modulators encompass 1,2 alkandiols, preferably selected from the group consisting of 1,2-pentandiol, 1,2 hexandiol, 1,2-heptandiol, 1,2-octandiol, 1,2-nonandiol, 1,2-decandiol, 1,2-undecandiol, 1,2-dodecandiol and their mixtures.

Preferably said 1,2-alkandiols are selected from 1,2-pentandiol, 1,2-hexandiol, 1,2-heptandiol, 1,2-octandiol and a mixture of 1,2-hexandiol and 1,2-octandiol.

Another group of suitable boosters forming group (b2) encompass polyols, selected from the group consisting of
glycerol;
1,2,ω-C4-C12-alkantriols, obtained from reaction products of 1,2-epoxy-ω-hydroxyalkanes with water;
technical oligoglycerol mixtures with a degree of self-condensation of 1.5 to 10, such as for example technical diglycerol mixtures with a diglycerol content of 40 to 50% by weight;
methylol compounds such as, in particular, trimethylol ethane, trimethylol propane, trimethylol butane, pentaerythritol and dipentaerythritol;
lower alkyl glucosides, particularly those containing 1 to 8 carbon atoms in the alkyl group, for example methyl and butyl glucoside;
sugar alcohols containing 5 to 12 carbon atoms, for example sorbitol or mannitol.
or their mixtures.

Blends

In a preferred embodiment said TRPV1 and/or TRPV3 modulators are selected from vanillyl ethers of formula (II) and said 1,2-alkandiols are selected from 1,2-hexandiol, 1,2-octandiol and their mixtures, and in particular said TRPV1 and/or TRPV3 modulator is vanillyl butyl ether and said 1,2-alkandiol are selected from 1,2-hexandiol, 1,2-octandiol and their mixtures.

The blends according to the present invention may comprise components (a) and (b) are present in a ratio by weight of from about 10:90 to about 90:10, preferably about 20:80 to about 80:20, and even more preferred about 30:70 to about 60:40. The overall preferred range is about 40:60. The blends may incorporate small amounts of stabilizers such as for example ascorbyl palmitate in amounts of from about 0.05 to 0.5% b.w., preferably of from 0.1 to about 0.2% b.w.

Cosmetic or Dermatological Compositions

Another object of the present invention relates to cosmetic or dermatological compositions comprising the blend of TRPV1/TRPV3 modulators and alkandiols as explained above, preferably in an amount suitable to effect warming sensation on human skin or mucous membranes, such as for example amounts of from 0.01 to about 5% b.w., preferably 0.1 to 2% b.w. and more preferred about 0.2 to about 1% b.w.—calculated on the final composition.

The preferred cosmetic or dermatological compositions are skin care or sun care compositions.

The preparations according to the invention may contain abrasives, anti-acne agents, agents against ageing of the skin, anti-cellulitis agents, antidandruff agents, anti-inflammatory agents, irritation-preventing agents, irritation-inhibiting agents, antioxidants, astringents, perspiration-inhibiting agents, antiseptic agents, anti-statics, binders, buffers, carrier materials, chelating agents, cell stimulants, cleansing agents, care agents, depilatory agents, surface-active substances, deodorizing agents, antiperspirants, softeners, emulsifiers, enzymes, essential oils, fibres, film-forming agents, fixatives, foam-forming agents, foam stabilizers, substances for preventing foaming, foam boosters, gelling agents, gel-forming agents, hair care agents, hair-setting agents, hair-straightening agents, moisture-donating agents, moisturizing substances, moisture-retaining substances, bleaching agents, strengthening agents, stain-removing agents, optically brightening agents, impregnating agents, dirt-repellent agents, friction-reducing agents, lubricants, moisturizing creams, ointments, opacifying agents, plasticizing agents, covering agents, polish, gloss agents, polymers, powders, proteins, re-oiling agents, abrading agents, silicones, skin-soothing agents, skin-cleansing agents, skin care agents, skin-healing agents, skin-lightening agents, skin-protecting agents, skin-softening agents, hair promotion agents, cooling agents, skin-cooling agents, warming agents, skin-warming agents, stabilizers, UV-absorbing agents, UV filters, detergents, fabric conditioning agents, suspending agents, skin-tanning agents, thickeners, vitamins, oils, waxes, fats, phospholipids, saturated fatty acids, mono- or polyunsaturated fatty acids, α-hydroxy acids, polyhydroxyfatty acids, liquefiers, dyestuffs, colour-protecting agents, pigments, anti-corrosives, aromas, flavouring substances, odoriferous substances, polyols, surfactants, electrolytes, organic solvents or silicone derivatives and the like as additional auxiliaries and additives.

Surfactans

Preferred auxiliaries and additives are anionic and/or amphoteric or zwitterionic surfactants. Typical examples of anionic surfactants are soaps, alkyl benzenesulfonates, alkanesulfonates, olefin sulfonates, alkylether sulfonates, glycerol ether sulfonates, methyl ester sulfonates, sulfofatty acids, alkyl sulfates, fatty alcohol ether sulfates, glycerol ether sulfates, fatty acid ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligoglucoside sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of amphoteric or zwitterionic surfactants are alkylbetaines, alkylamidobetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineralöladditive (Catalysts, Surfactants and Mineral Oil Additives)", Thieme Verlag, Stuttgart, 1978, pages 123-217. The percentage content of surfactants in the preparations may be from 0.1 to 10% by weight and is preferably from 0.5 to 5% by weight, based on the preparation.

Oil Bodies

Suitable oil bodies, which form constituents of the O/W emulsions, are, for example, Guerbet alcohols based on fatty alcohols having 6 to 18, preferably 8 to 10, carbon atoms, esters of linear $C_6$-$C_{22}$-fatty acids with linear or branched $C_6$-$C_{22}$-fatty alcohols or esters of branched $C_6$-$C_{13}$-carboxylic acids with linear or branched $C_6$-$C_{22}$-fatty alcohols, such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. Also suitable are esters of linear $C_6$-$C_{22}$-fatty acids with branched alcohols, in particular 2-ethylhexanol, esters of $C_{18}$-$C_{38}$-alkylhydroxy carboxylic acids with linear or branched $C_6$-$C_{22}$-fatty alcohols, in particular Dioctyl Malate, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{11}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear and branched $C_6$-$C_{22}$-fatty alcohol carbonates, such as, for example, Dicaprylyl Carbonate (Cetiol® CC), Guerbet carbonates, based on fatty alcohols having 6 to 18, preferably 8 to 10, carbon atoms, esters of benzoic acid with linear and/or branched $C_6$-$C_{22}$-alcohols (e.g. Finsolv® TN), linear or branched, symmetrical or asymmetrical dialkyl ethers having 6 to 22 carbon atoms per alkyl group, such as, for example, dicaprylyl ether (Cetiol® OE), ring-opening products of epoxidized fatty acid esters with polyols, silicone oils (cyclomethicones, silicone methicone grades, etc.) and/or aliphatic or naphthenic hydrocarbons, such as, for example, squalane, squalene or dialkylcyclohexanes.

Emulsifiers

Other surfactants may also be added to the preparations as emulsifiers, including for example:
   products of the addition of 2 to 30 mol ethylene oxide and/or 0 to 5 mol propylene oxide onto linear $C_{8-22}$ fatty alcohols, onto $C_{12-22}$ fatty acids and onto alkyl phenols containing 8 to 15 carbon atoms in the alkyl group;
   $C_{12/18}$ fatty acid monoesters and diesters of addition products of 1 to 30 mol ethylene oxide onto glycerol;

glycerol mono- and diesters and sorbitan mono- and diesters of saturated and unsaturated fatty acids containing 6 to 22 carbon atoms and ethylene oxide addition products thereof;

addition products of 15 to 60 mol ethylene oxide onto castor oil and/or hydrogenated castor oil;

polyol esters and, in particular, polyglycerol esters such as, for example, polyglycerol polyricinoleate, polyglycerol poly-12-hydroxystearate or polyglycerol dimerate isostearate. Mixtures of compounds from several of these classes are also suitable;

addition products of 2 to 15 mol ethylene oxide onto castor oil and/or hydrogenated castor oil;

partial esters based on linear, branched, unsaturated or saturated $C_{6/22}$ fatty acids, ricinoleic acid and 12-hydroxystearic acid and glycerol, polyglycerol, pentaerythritol, -dipentaerythritol, sugar alcohols (for example sorbitol), alkyl glucosides (for example methyl glucoside, butyl glucoside, lauryl glucoside) and polyglucosides (for example cellulose);

mono-, di and trialkyl phosphates and mono-, di- and/or tri-PEG-alkyl phosphates and salts thereof;

wool wax alcohols;

polysiloxane/polyalkyl polyether copolymers and corresponding derivatives;

mixed esters of pentaerythritol, fatty acids, citric acid and fatty alcohol and/or mixed esters of $C_{6-22}$ fatty acids, methyl glucose and polyols, preferably glycerol or polyglycerol, polyalkylene glycols and glycerol carbonate.

The addition products of ethylene oxide and/or propylene oxide onto fatty alcohols, fatty acids, alkylphenols, glycerol mono- and diesters and sorbitan mono- and diesters of fatty acids or onto castor oil are known commercially available products. They are homologue mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide onto glycerol are known as lipid layer enhancers for cosmetic formulations. The preferred emulsifiers are described in more detail as follows:

Partial glycerides. Typical examples of suitable partial glycerides are hydroxystearic acid monoglyceride, hydroxystearic acid diglyceride, isostearic acid monoglyceride, isostearic acid diglyceride, oleic acid monoglyceride, oleic acid diglyceride, ricinoleic acid monoglyceride, ricinoleic acid diglyceride, linoleic acid monoglyceride, linoleic acid diglyceride, linolenic acid monoglyceride, linolenic acid diglyceride, erucic acid monoglyceride, erucic acid diglyceride, tartaric acid monoglyceride, tartaric acid diglyceride, citric acid monoglyceride, citric acid diglyceride, malic acid monoglyceride, malic acid diglyceride and technical mixtures thereof which may still contain small quantities of triglyceride from the production process. Addition products of 1 to 30 and preferably 5 to 10 mol ethylene oxide onto the partial glycerides mentioned are also suitable.

Sorbitan esters. Suitable sorbitan esters are sorbitan monoisostearate, sorbitan sesquiisostearate, sorbitan diisostearate, sorbitan triisostearate, sorbitan monooleate, sorbitan sesquioleate, sorbitan dioleate, sorbitan trioleate, sorbitan monoerucate, sorbitan sesquierucate, sorbitan dierucate, sorbitan trierucate, sorbitan monoricinoleate, sorbitan sesquiricinoleate, sorbitan diricinoleate, sorbitan triricinoleate, sorbitan monohydroxystearate, sorbitan sesquihydroxystearate, sorbitan dihydroxystearate, sorbitan trihydroxystearate, sorbitan monotartrate, sorbitan sesquitartrate, sorbitan ditartrate, sorbitan tritartrate, sorbitan monocitrate, sorbitan sesquicitrate, sorbitan dicitrate, sorbitan tricitrate, sorbitan monomaleate, sorbitan sesquimaleate, sorbitan dimaleate, sorbitan trimaleate and technical mixtures thereof. Addition products of 1 to 30 and preferably 5 to 10 mol ethylene oxide onto the sorbitan esters mentioned are also suitable.

Polyglycerol esters. Typical examples of suitable polyglycerol esters are Polyglyceryl-2 Dipolyhydroxystearate (Dehymuls® PGPH), Polyglycerin-3-Diisostearate (Lameform® TGI), Polyglyceryl-4 Isostearate (Isolan® GI 34), Polyglyceryl-3 Oleate, Diisostearoyl Polyglyceryl-3 Diisostearate (Isolan® PDI), Polyglyceryl-3 Methylglucose Distearate (Tego Care® 450), Polyglyceryl-3 Beeswax (Cera Bellina®), Polyglyceryl-4 Caprate (Polyglycerol Caprate T2010/90), Polyglyceryl-3 Cetyl Ether (Chimexane® NL), Polyglyceryl-3 Distearate (Cremophor® GS 32) and Polyglyceryl Polyricinoleate (Admul® WOL 1403), Polyglyceryl Dimerate Isostearate and mixtures thereof. Examples of other suitable polyolesters are the mono-, di- and triesters of trimethylol propane or pentaerythritol with lauric acid, cocofatty acid, tallow fatty acid, palmitic acid, stearic acid, oleic acid, behenic acid and the like optionally reacted with 1 to 30 mol ethylene oxide.

Anionic emulsifiers. Typical anionic emulsifiers are aliphatic $C_{12-22}$ fatty acids, such as palmitic acid, stearic acid or behenic acid for example, and $C_{12-22}$ dicarboxylic acids, such as azelaic acid or sebacic acid for example.

Amphoteric emulsifiers. Other suitable emulsifiers are amphboteric or zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example coco-acylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting Agents and Consistency Factors

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers.

The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-12-hydroxystearates is preferably used.

Thickening Agents and Rheology Additives

Suitable thickeners are polymeric thickeners, such as Aerosil® types (hydrophilic silicas), polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates and electrolytes, such as sodium chloride and ammonium chloride.

Polymers

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau), quaternized wheat polypeptides, polyethyleneimine, cationic silicone polymers such as, for example, amodimethicone, copolymers of adipic acid and dimethylaminohy-droxypropyl diethylenetriamine (Cartaretine®, Sandoz), copolymers of acrylic acid with dimethyl diallyl ammonium chloride (Merquat® 550, Chemviron), polyaminopolyamides and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar° C.-16 of Celanese, quaternized ammonium salt polymers such as, for example, Mirapol® A-15, Mirapol® AD-1, Mirapol® AZ-1 of Miranol and the various polyquaternium types (for example 6, 7, 32 or 37) which can be found in the market under the tradenames Rheocare® CC or Ultragel® 300.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert-butylaminoethyl methacrylate/2-hydroxypropyl methacrylate copolymers, polyvinyl pyrrolidone, vinyl pyrrolidone/vinyl acetate copolymers, vinyl pyrrolidone/dimethylaminoethyl methacrylate/vinyl caprolactam terpolymers and optionally derivatized cellulose ethers and silicones.

Pearlizing Waxes

Suitable pearlising waxes are, for example, alkylene glycol esters, especially ethylene glycol distearate; fatty acid alkanolamides, especially cocofatty acid diethanolamide; partial glycerides, especially stearic acid monoglyceride; esters of polybasic, optionally hydroxy-substituted carboxylic acids with fatty alcohols containing 6 to 22 carbon atoms, especially long-chain esters of tartaric acid; fatty compounds, such as for example fatty alcohols, fatty ketones, fatty aldehydes, fatty ethers and fatty carbonates which contain in all at least 24 carbon atoms, especially laurone and distearylether; fatty acids, such as stearic acid, hydroxystearic acid or behenic acid, ring opening products of olefin epoxides containing 12 to 22 carbon atoms with fatty alcohols containing 12 to 22 carbon atoms and/or polyols containing 2 to 15 carbon atoms and 2 to 10 hydroxyl groups and mixtures thereof.

Silicones

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Other suitable silicone compounds are simethicones which are mixtures of dimethicones with an average chain length of 200 to 300 dimethylsiloxane units and hydrogenated silicates. A detailed overview of suitable volatile silicones can be found in Todd et al. in Cosm. Toil. 91, 27 (1976).

Waxes and Stabilizers

Besides natural oils used, waxes may also be present in the preparations, more especially natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes and micro-waxes; chemically modified waxes (hard waxes) such as, for example, montan ester waxes, sasol waxes, hydrogenated jojoba waxes and synthetic waxes such as, for example, polyalkylene waxes and polyethylene glycol waxes.

Metal salts of fatty acids such as, for example, magnesium, aluminium and/or zinc stearate or ricinoleate may be used as stabilizers.

Primary Sun Protection Factors

Primary sun protection factors in the context of the invention are, for example, organic substances (light filters) which are liquid or crystalline at room temperature and which are capable of absorbing ultraviolet radiation and of releasing the energy absorbed in the form of longer-wave radiation, for example heat.

The formulations according to the invention advantageously contain at least one UV-A filter and/or at least one UV-B filter and/or a broadband filter and/or at least one inorganic pigment. Formulations according to the invention preferably contain at least one UV-B filter or a broadband filter, more particularly preferably at least one UV-A filter and at least one UV-B filter.

Preferred cosmetic compositions, preferably topical formulations according to the present invention comprise one, two, three or more sun protection factors selected from the group consisting of 4-aminobenzoic acid and derivatives, salicylic acid derivatives, benzophenone derivatives, dibenzoylmethane derivatives, diphenyl acrylates, 3-imidazol-4-yl acrylic acid and esters thereof, benzofuran derivatives, benzylidene malonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenylbenzimidazole sulfonic acid derivatives and salts thereof, anthranilic acid menthyl esters, benzotriazole derivativesand indole derivatives.

In addition, it is advantageous to combine compounds of formula (I) with active ingredients which penetrate into the skin and protect the skin cells from inside against sunlight-induced damage and reduce the level of cutaneous matrix metalloproteases. Preferred respective ingredients, so called arylhydrocarbon receptor antagonists, are described in WO 2007/128723, incorporated herein by reference. Preferred is 2-benzylidene-5,6-dimethoxy-3,3-dimethylindan-1-one.

The UV filters cited below which can be used within the context of the present invention are preferred but naturally are not limiting.

UV filters which are preferably used are selected from the group consisting of
- p-aminobenzoic acid
- p-aminobenzoic acid ethyl ester (25 mol) ethoxylated (INCI name: PEG-25 PABA)
- p-dimethylaminobenzoic acid-2-ethylhexyl ester
- p-aminobenzoic acid ethyl ester (2 mol) N-propoxylated
- p-aminobenzoic acid glycerol ester
- salicylic acid homomenthyl ester (homosalates) (Neo Heliopan®HMS)
- salicylic acid-2-ethylhexyl ester (Neo Heliopan®OS)
- triethanolamine salicylate
- 4-isopropyl benzyl salicylate
- anthranilic acid menthyl ester (Neo Heliopan®MA)
- diisopropyl cinnamic acid ethyl ester
- p-methoxycinnamic acid-2-ethylhexyl ester (Neo Heliopan®AV)
- diisopropyl cinnamic acid methyl ester
- p-methoxycinnamic acid isoamyl ester (Neo Heliopan®E 1000)
- p-methoxycinnamic acid diethanolamine salt
- p-methoxycinnamic acid isopropyl ester
- 2-phenylbenzimidazole sulfonic acid and salts (Neo Heliopan Hydro)
- 3-(4'-trimethylammonium) benzylidene bornan-2-one methyl sulfate
- beta-imidazole-4(5)-acrylic acid (urocanic acid)
- 3-(4'-sulfo)benzylidene bornan-2-one and salts
- 3-(4'-methyl benzylidene)-D,L-camphor (Neo Heliopan MBC)
- 3-benzylidene-D,L-camphor
- N-[(2 and 4)-[2-(oxoborn-3-ylidene)methyl]benzyl] acrylamide polymer
- 4,4'-[(6-[4-(1,1-dimethyl)aminocarbonyl) phenylamino]-1,3,5-triazine-2,4-diyl)diimino]-bis-(benzoic acid-2-ethylhexyl ester) (Uvasorb®HEB)
- benzylidene malonate polysiloxane (Parsol SLX)
- glyceryl ethylhexanoate dimethoxycinnamate
- dipropylene glycol salicylate
- tris(2-ethylhexyl)-4,4',4"-(1,3,5-triazine-2,4,6-triyl-triimino)tribenzoate (=2,4,6-trianilino-(p-carbo-2'-ethylhexyl-1'-oxy)-1,3,5-triazine) (Uvinul®T150).

Broadband filters which are preferably combined with one or more compounds of formula (I) in a preparation according to the present invention are selected from the group consisting of
- 2-ethylhexyl-2-cyano-3,3-diphenyl acrylate (Neo Heliopan®303)
- ethyl-2-cyano-3,3'-diphenyl acrylate
- 2-hydroxy-4-methoxybenzophenone (Neo Heliopan®BB)
- 2-hydroxy-4-methoxybenzophenone-5-sulfonic acid
- dihydroxy-4-methoxybenzophenone
- 2,4-dihydroxybenzophenone
- tetrahydroxybenzophenone
- 2,2'-dihydroxy-4,4'-dimethoxybenzophenone
- 2-hydroxy-4-n-octoxybenzophenone
- 2-hydroxy-4-methoxy-4'-methyl benzophenone
- sodium hydroxymethoxybenzophenone sulfonate
- disodium-2,2'-dihydroxy-4,4'-dimethoxy-5,5'-disulfobenzophenone
- phenol, 2-(2H-benzotriazol-2-yl)-4-methyl-6-(2-methyl-3 (1,3,3,3-tetramethyl-1-(trimethylsilyl)oxy)disiloxanyl)propyl) (Mexoryl®XL)
- 2,2'-methylene bis-(6-(2H-benzotriazol-2-yl)-4-1,1,3,3-tetramethylbutyl)phenol) (Tinosorb®M)
- 2,4-bis[4-(2-ethylhexyloxy)-2-hydroxyphenyl]-1,3,5-triazine
- 2,4-bis-[{(4-(2-ethylhexyloxy)-2-hydroxy}phenyl]-6-(4-methoxyphenyl)-1,3,5-triazine (Tinosorb®S)
- 2,4-bis-[{(4-(3-sulfonato)-2-hydroxypropyloxy)-2-hydroxy}phenyl]-6-(4-methoxyphenyl)-1,3,5-triazine sodium salt
- 2,4-bis-[{(3-(2-propyloxy)-2-hydroxypropyloxy)-2-hydroxy}phenyl]-6-(4-methoxyphenyl)-1,3,5-triazine
- 2,4-bis-[{4-(2-ethylhexyloxy)-2-hydroxy}phenyl]-6-[4-(2-methoxyethyl carbonyl) phenylamino]-1,3,5-triazine
- 2,4-bis-[{4-(3-(2-propyloxy)-2-hydroxypropyloxy)-2-hydroxy}phenyl]-6-[4-(2-ethylcarboxyl)phenylamino]-1,3,5-triazine
- 2,4-bis-[{4-(2-ethylhexyloxy)-2-hydroxy}phenyl]-6-(1-methylpyrrol-2-yl)-1,3,5-triazine
- 2,4-bis-[{4-tris-(trimethylsiloxysilylpropyloxy)-2-hydroxy}phenyl]-6-(4-methoxyphenyl)-1,3,5-triazine
- 2,4-bis-[{4-(2"-methylpropenyloxy)-2-hydroxy}phenyl]-6-(4-methoxyphenyl)-1,3,5-triazine
- 2,4-bis-[{4-(1',1',1',3',5',5',5'-heptamethylsiloxy-2"-methylpropyloxy)-2-hydroxy}phenyl]-6-(4-methoxyphenyl)-1,3,5-triazine.

The compositions can comprise further typical detergent and cleansing composition ingredients such as UV-A filters filters which are preferably combined with one or more compounds of formula (I) in a preparation according to the present invention are selected from the group consisting of
- 4-isopropyl dibenzoyl methane
- terephthalylidene dibornane sulfonic acid and salts (Mexoryl®SX)
- 4-t-butyl-4'-methoxydibenzoyl methane (avobenzone)/ (Neo Heliopan®357)
- phenylene bis-benzimidazyl tetrasulfonic acid disodium salt (Neo Heliopan®AP)
- 2,2'-(1,4-phenylene)-bis-(1H-benzimidazole-4,6-disulfonic acid), monosodium salt
- 2-(4-diethylamino-2-hydroxybenzoyl)benzoic acid hexyl ester (Uvinul® A Plus)
- indanylidene compounds in accordance with DE 100 55 940 A1 (=WO 2002 038537 A1)

The compositions can comprise further typical detergent and cleansing composition ingredients such as UV filters which are more preferably combined with one or more compounds of formula (I) in a preparation according to the present invention are selected from the group consisting of
- p-aminobenzoic acid
- 3-(4'-trimethylammonium)benzylidene bornan-2-one methyl sulfate
- salicylic acid homomenthyl ester (Neo Heliopan®HMS)
- 2-hydroxy-4-methoxybenzophenone (Neo Heliopan®1313)
- 2-phenylbenzimidazole sulfonic acid (Neo Heliopan®Hydro)
- terephthalylidene dibornane sulfonic acid and salts (Mexoryl®SX)

4-tert-butyl-4'-methoxydibenzoyl methane (Neo Heliopan®357)
3-(4'-sulfo)benzylidene bornan-2-one and salts
2-ethylhexyl-2-cyano-3,3-diphenyl acrylate (Neo Heliopan®303)
N-[(2 and 4)-[2-(oxoborn-3-ylidene)methyl]benzyl]acrylamide polymer
p-methoxycinnamic acid-2-ethylhexyl ester (Neo Heliopan®AV)
p-aminobenzoic acid ethyl ester (25 mol) ethoxylated (INCI name: PEG-25 PABA)
p-methoxycinnamic acid isoamyl ester (Neo Heliopan®E1000)
2,4,6-trianilino-(p-carbo-2'-ethylhexyl-1'-oxy)-1,3,5-triazine (Uvinul®T150)
phenol, 2-(2H-benzotriazol-2-yl)-4-methyl-6-(2-methyl-3 (1,3,3,3-tetramethyl-1-(trimethylsilyl)oxy)disiloxanyl)propyl) (Mexoryl®XL)
4,4'-[(6-[4-(1,1-dimethyl)aminocarbonyl)phenylamino]-1,3,5-triazine-2,4-diyl)diimino]-bis-(benzoic acid-2-ethylhexyl ester) (Uvasorb HEB)
3-(4'-methyl benzylidene)-D,L-camphor (Neo Heliopan®MBC)
3-benzylidene camphor
salicylic acid-2-ethylhexyl ester (Neo Heliopan®OS)
4-dimethylaminobenzoic acid-2-ethylhexyl ester (Padimate O)
hydroxy-4-methoxybenzophenone-5-sulfonic acid and Na salt
2,2'-methylene bis-(6-(2H-benzotriazol-2-yl)-4-1,1,3,3-tetramethylbutyl)phenol) (Tinosorb®M)
phenylene bis-benzimidazyl tetrasulfonic acid disodium salt (Neo Heliopan®AP)
2,4-bis-[{(4-(2-ethylhexyloxy)-2-hydroxy}phenyl]-6-(4-methoxyphenyl)-1,3,5-triazine (Tinosorb®S)
benzylidene malonate polysiloxane (Parsol®SLX)
menthyl anthranilate (Neo Heliopan®MA)
2-(4-diethylamino-2-hydroxybenzoyl) benzoic acid hexyl ester (Uvinul® A Plus)
indanylidene compounds in accordance with DE 100 55 940 (=WO 02/38537).

Advantageous primary and also secondary sun protection factors are mentioned in WO 2005 123101 A1. Advantageously, these preparations contain at least one UVA filter and/or at least one UVB filter and/or at least one inorganic pigment. The preparations may be present here in various forms such as are conventionally used for sun protection preparations. Thus, they may be in form of a solution, an emulsion of the water-in-oil type (W/O) or of the oil-in-water type (O/W) or a multiple emulsion, for example of the water-in-oil-in-water type (W/O/W), a gel, a hydrodispersion, a solid stick or else an aerosol.

In a further preferred embodiment a formulation according to the invention contains a total amount of sunscreen agents, i.e. in particular UV filters and/or inorganic pigments (UV filtering pigments) so that the formulation according to the invention has a light protection factor of greater than or equal to 2 (preferably greater than or equal to 5). Such formulations according to the invention are particularly suitable for protecting the skin and hair.

Secondary Sun Protection Factors

Besides the groups of primary sun protection factors mentioned above, secondary sun protection factors of the antioxidant type may also be used. Secondary sun protection factors of the antioxidant type interrupt the photochemical reaction chain which is initiated when UV rays penetrate into the skin. Typical examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example alpha-carotene, beta-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, alpha-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages, also (metal) chelators (for example alpha-hydroxyfatty acids, palmitic acid, phytic acid, lactoferrine), alpha-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, superoxide dismutase, titanium dioxide (for example dispersions in ethanol), zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Advantageous inorganic secondary light protection pigments are finely dispersed metal oxides and metal salts which are also mentioned in WO 2005 123101 A1. The total quantity of inorganic pigments, in particular hydrophobic inorganic micro-pigments in the finished cosmetic preparation according to the present invention is advantageously from 0.1 to 30% by weight, preferably 0.5 to 10.0% by weight, in each case based on the total weight of the preparation.

Also preferred are particulate UV filters or inorganic pigments, which can optionally be hydrophobed, can be used, such as the oxides of titanium ($TiO_2$), zinc (ZnO), iron ($Fe_2O_3$), zirconium ($ZrO_2$), silicon ($SiO_2$), manganese (e.g. MnO), aluminium ($Al_2O_3$), cerium (e.g. $Ce_2O_3$) and/or mixtures thereof.

Actives Modulating Skin Pigmentation

Preferred active ingredients for skin and/or hair lightening are selected from the group consisting of: kojic acid (5-hydroxy-2-hydroxymethyl-4-pyranone), kojic acid derivatives, preferably kojic acid dipalmitate, arbutin, ascorbic acid, ascorbic acid derivatives, preferably magnesium ascorbyl phosphate, hydroquinone, hydroquinone derivatives, resorcinol, resorcinol derivatives, preferably 4-alkylresorcinols and 4-(1-phenylethyl)1,3-dihydroxybenzene (phenylethyl resorcinol), cyclohexylcarbamates (preferably one or more cyclohexyl carbamates disclosed in WO 2010/122178 and WO 2010/097480), sulfur-containing molecules, preferably glutathione or cysteine, alpha-hydroxy acids (preferably citric acid, lactic acid, malic acid), salts and esters thereof, N-acetyl tyrosine and derivatives, undecenoyl phenylalanine, gluconic acid, chromone derivatives, preferably aloesin, flavonoids, 1-aminoethyl phosphinic acid, thiourea derivatives, ellagic acid, nicotinamide (niacinamide), zinc salts, preferably zinc chloride or zinc gluconate, thujaplicin and derivatives, triterpenes, preferably maslinic acid, sterols, preferably ergosterol, benzofuranones, preferably senkyunolide, vinyl guiacol, ethyl guiacol, dionic acids, preferably octodecene dionic acid and/or azelaic acid, inhibitors of nitrogen oxide synthesis, preferably L-nitroarginine and derivatives thereof, 2,7-dinitroindazole or thiocitrulline, metal chelators (preferably alpha-hydroxy fatty acids, phytic acid, humic acid, bile acid, bile extracts, EDTA, EGTA and derivatives thereof), retinoids, soy milk and extract, serine protease inhibitors or lipoic acid or other synthetic or natural active ingredients for skin and hair lightening, the latter preferably used in the form of an extract from plants, preferably bearberry extract, rice extract, papaya extract, turmeric extract, mulberry extract, bengkoang extract, nutgrass extract, liquorice root extract or constituents concentrated or isolated therefrom, preferably glabridin or licochalcone A, artocarpus extract, extract of rumex and ramulus species, extracts of pine species (pinus), extracts of vitis species or stilbene derivatives isolated or concentrated therefrom, saxifrage extract, scutelleria extract, grape extract and/or microalgae extract, in particular Tetraselmis suecica Extract.

Preferred skin lighteners as component (b) are kojic acid and phenylethyl resorcinol as tyrosinase inhibitors, beta- and alpha-arbutin, hydroquinone, nicotinamide, dioic acid, Mg ascorbyl phosphate and vitamin C and its derivatives, mulberry extract, Bengkoang extract, papaya extract, turmeric extract, nutgrass extract, licorice extract (containing glycyrrhizin), alpha-hydroxy-acids, 4-alkylresorcinols, 4-hydroxyanisole. These skin lighteners are preferred due to their very good activity, in particular in combination with sclareolide according to the present invention. In addition, said preferred skin lighteners are readily available.

Advantageous skin and hair tanning active ingredients in this respect are substrates or substrate analogues of tyrosinase such as L-tyrosine, N-acetyl tyrosine, L-DOPA or L-dihydroxyphenylalanine, xanthine alkaloids such as caffeine, theobromine and theophyl-line and derivatives thereof, proopiomelanocortin peptides such as ACTH, alpha-MSH, peptide analogues thereof and other substances which bind to the melanocortin receptor, peptides such as Val-Gly-Val-Ala-Pro-Gly, Lys-Ile-Gly-Arg-Lys or Leu-Ile-Gly-Lys, purines, pyrimidines, folic acid, copper salts such as copper gluconate, chloride or pyrrolidonate, 1,3,4-oxadiazole-2-thiols such as 5-pyrazin-2-yl-1,3,4-oxadiazole-2-thiol, curcumin, zinc diglycinate (Zn(Gly)2), manganese(II) bicarbonate complexes ("pseudocat-alases") as described for example in EP 0 584 178, tetrasubstituted cyclohexene deriva-tives as described for example in WO 2005/032501, isoprenoids as described in WO 2005/102252 and in WO 2006/010661, melanin derivatives such as Melasyn-100 and MelanZe, diacyl glycerols, aliphatic or cyclic diols, psoralens, prostaglandins and ana-logues thereof, activators of adenylate cyclase and compounds which activate the transfer of melanosomes to keratinocytes such as serine proteases or agonists of the PAR-2 receptor, extracts of plants and plant parts of the chrysanthemum species, san-guisorba species, walnut extracts, urucum extracts, rhubarb extracts, microalgae extracts, in particular Isochrysis galbana, trehalose, erythru-lose and dihydroxyacetone. Flavonoids which bring about skin and hair tinting or brown-ing (e.g. quercetin, rhamnetin, kaempferol, fisetin, genistein, daidzein, chrysin and apigenin, epicatechin, diosmin and diosmetin, morin, quercitrin, naringenin, hesperidin, phloridzin and phloretin) can also be used.

The amount of the aforementioned examples of additional active ingredients for the modulation of skin and hair pigmentation (one or more compounds) in the products according to the invention is then preferably 0.00001 to 30 wt. %, preferably 0.0001 to 20 wt. %, particularly preferably 0.001 to 5 wt. %, based on the total weight of the preparation.

Anti-Ageing Actives

In the context of the invention, anti-ageing or biogenic agents are, for example antioxidants, matrix-metalloproteinase inhibitors (MMPI), skin moisturizing agents, glycosaminglycan stimulators, anti-inflammatory agents, TRPV1 antagonists and plant extracts.

Antioxidants. Suitable antioxidants encompass amino acids (preferably glycine, histidine, tyrosine, tryptophane) and derivatives thereof, imidazoles (preferably urocanic acid) and derivatives thereof, peptides, preferably D,L-carnosine, D-carnosine, L-carnosine and derivatives thereof (preferably anserine), carnitine, creatine, matrikine peptides (preferably lysyl-threonyl-threonyl-lysyl-serine) and palmitoylated pentapeptides, carotenoids, carotenes (preferably alpha-carotene, beta-carotene, lycopene) and derivatives thereof, lipoic acid and derivatives thereof (preferably dihydrolipoic acid), aurothioglucose, propyl thiouracil and other thiols (preferably thioredoxine, glutathione, cysteine, cystine, cystamine and glycosyl, N-acetyl, methyl, ethyl, propyl, amyl, butyl and lauryl, palmitoyl, oleyl, gamma-linoleyl, cholesteryl, glyceryl and oligoglyceryl esters thereof) and salts thereof, dilauryl thiodipropionate, distearyl thiodipropionate, thiodipropionic acid and derivatives thereof (preferably esters, ethers, peptides, Ddpeptides, dragosine, TPI peptides (as for example Sympeptide226, Sympeptide235, Sympeptide 222, Sympeptide 230, Sympeptide 225, Sympeptide 245, Sympeptide 239,Retinopeptide189) lipids, nucleotides, nucleosides and salts) and sulfoximine compounds (preferably buthionine sulfoximines, homocysteine sulfoximine, buthionine sulfones, penta-, hexa-, heptathionine sulfoximine) in very small tolerated doses (e.g. pmol to µmol/kg), also (metal) chelators (preferably alpha-hydroxy fatty acids, palmitic acid, phytic acid, lactoferrin, alpha-hydroxy acids (preferably citric acid, lactic acid, malic acid), humic acid, bile acid, bile extracts, tannins, bilirubin, biliverdin, EDTA, EGTA and derivatives thereof), unsaturated fatty acids and derivatives thereof (preferably gamma-linolenic acid, linoleic acid, oleic acid), folic acid and derivatives thereof, ubiquinone and derivatives thereof, ubiquinol and derivatives thereof, vitamin C and derivatives (preferably ascorbyl palmitate, Mg ascorbyl phosphate, ascorbyl acetate, ascorbyl glucoside), tocopherols and derivatives (preferably vitamin E acetate), vitamin A and derivatives (vitamin A palmitate, retinoic acid, 2-(4-methoxyphenyl)-2-oxoethyl ester, 13-cis-, (3,3-dimethyl-2-oxo-butyl) (2E,4E,6E,8E)-3,7-dimethyl-9-(2,6,6-trimethyl-cyclohexen-1-yl)nona-2,4,6,8-tetraenoate) and coniferyl benzoate of benzoic resin, rutinic acid and derivatives thereof, flavonoids and glycosylated precursors thereof, in particular quercetin and derivatives thereof, preferably alpha-glucosyl rutin, rosmarinic acid, carnosol, carnosolic acid, resveratrol, caffeic acid and derivatives thereof, sinapic acid and derivatives thereof, ferulic acid and derivatives thereof, curcuminoids, chlorogenic acid and derivatives thereof, retinoids, preferably retinyl palmitate, retinol or tretinoin, ursolic acid, levulinic acid, butyl hydroxytoluene, butyl hydroxyanisole, nordihydroguaiac acid, nordihydroguaiaretic acid, trihydroxybutyrophenone, uric acid and derivatives thereof, mannose and derivatives thereof, zinc and derivatives thereof (preferably ZnO, $ZnSO_4$), selenium and derivatives thereof (preferably selenium methionine), superoxide dismutase, stilbenes and derivatives thereof (preferably stilbene oxide, trans-stilbene oxide) and the derivatives (salts, esters, ethers, sugars, nucleotides, nucleosides, peptides and lipids) of these cited active ingredients which are suitable according to the invention or extracts or fractions of plants having an antioxidant effect, preferably green tea, rooibos, honeybush, grape, rosemary, sage, melissa, thyme, lavender, olive, oats, cocoa, ginkgo, ginseng, liquorice, honeysuckle, sophora, pueraria, pinus, citrus, Phyllanthus emblica or St. John's wort, grape seeds, wheat germ, Phyllanthus emblica, coenzymes, preferably coenzyme Q10, plastoquinone and menaquinone. Preferred antioxidants are selected from the group consisting of vitamin A and derivatives, vitamin C and derivatives, tocopherol and derivatives, preferably tocopheryl acetate, and ubiquinone.

If vitamin E and/or derivatives thereof are used as the antioxidant(s), it is advantageous to choose their concentrations from the range from about 0.001 to about 10% b.w. based on the total weight of the formulation. If vitamin A or vitamin A derivatives or carotenes or derivatives thereof are used as the antioxidant(s), it is advantageous to choose their concentrations from the range from about 0.001 to about 10% b.w. based on the total weight of the formulation.

Matrix-Metalloproteinase inhibitors (MMPI). Preferred compositions comprise matrix-metalloproteinase inhibitors, especially those inhibiting matrix-metalloproteinases enzymatically cleaving collagen, selected from the group consisting of: ursolic acid, retinyl palmitate, propyl gallate, precocenes, 6-hydroxy-7-methoxy-2,2-dimethyl-1(2H)-benzopyran, 3,4-dihydro-6-hydroxy-7-methoxy-2,2-dimethyl-1(2H)-benzopyran, benzamidine hydrochloride, the cysteine proteinase inhibitors N-ethylmalemide and epsilon-amino-n-caproic acid of the serinprotease inhibitors: phenylmethylsufonylfluoride, collhibin (company Pentapharm; INCI: hydrolysed rice protein), oenotherol (company Soliance; INCI: propylene glycol, aqua, Oenothera biennis root extract, ellagic acid and ellagitannins, for example from pomegranate), phosphoramidone hinokitiol, EDTA, galardin, EquiStat (company Collaborative Group; apple fruit extract, soya seed extract, ursolic acid, soya isoflavones and soya proteins), sage extracts, MDI (company Atrium; INCI: glycosaminoglycans), fermiskin (company Silab/Mawi; INCI: water and lentinus edodes extract), actimp 1.9.3 (company Expanscience/Rahn; INCI: hydrolysed lupine protein), lipobelle soyaglycone (company Mibelle; INCI: alcohol, polysorbate 80, lecithin and soy isoflavones), extracts from green and black tea and further plant extracts, which are listed in WO 02 069992 A1 (see tables 1-12 there, incorporated herein by reference), proteins or glycoproteins from soya, hydrolysed proteins from rice, pea or lupine, plant extracts which inhibit MMPs, preferably extracts from shitake mushrooms, extracts from the leaves of the Rosaceae family, sub-family Rosoideae, quite particularly extracts of blackberry leaf (preferably as described in WO 2005 123101 A1, incorporated herein by reference) as e.g. SymMatrix (company Symrise, INCI: Maltodextrin, Rubus Fruticosus (Blackberry) Leaf Extract). Preferred actives of are selected from the group consisting of retinyl palmitate, ursolic acid, extracts from the leaves of the Rosaceae family, sub-family Rosoideae, genistein and daidzein.

Skin-moisturizing agents. Preferred skin moisturizing agents are selected from the group consisting of Hydroviton24Plus, urea, sodium pyrrolidon carboxylic acids, sugars, Ggycerin, and amino acids.

Glycosaminoglycan stimulators. Preferred compositions comprise substances stimulating the synthesis of glycosaminoglycans selected from the group consisting of hyaluronic acid and derivatives or salts, Subliskin (Sederma, INCI: Sinorhizobium Meliloti Ferment Filtrate, Cetyl Hydroxyethylcellulose, Lecithin), Hyalufix (BASF, INCI: Water, Butylene Glycol, Alpinia galanga leaf extract, Xanthan Gum, Caprylic/Capric Triglyceride), Stimulhyal (Soliance, INCI: Calcium ketogluconate), Syn-Glycan (DSM, INCI: Tetradecyl Aminobutyroylvalylaminobutyric Urea Trifluoroacetate, Glycerin, Magnesium chloride), Kalpariane (Biotech Marine), DC Upregulex (Distinctive Cosmetic Ingredients, INCI: Water, Butylene Glycol, Phospholipids, Hydrolyzed Sericin), glucosamine, N-acetyl glucosamine, retinoids, preferably retinol and vitamin A, Arctium lappa fruit extract, Eriobotrya japonica extract, Genkwanin, N-Methyl-L-serine, (−)-alpha-bisabolol or synthetic alpha-bisabolol such as e.g. Dragosantol and Dragosantol 100 from Sym rise, oat glucan, Echinacea purpurea extract and soy protein hydrolysate. Preferred actives are selected from the group consisting of hyaluronic acid and derivatives or salts, retinol and derivatives, (−)-alpha-bisabolol or synthetic alpha-bisabolol such as e.g. Dragosantol and Dragosantol 100 from Symrise, oat glucan, Echinacea purpurea extract, Sinorhizobium Meliloti Ferment Filtrate, Calcium ketogluconate, Alpinia galanga leaf extract and tetradecyl aminobutyroylvalylaminobutyric urea trifluoroacetate.

In case ginger extract is used in the context of the present invention, preferably extracts of the fresh or dried ginger root are used which are prepared by extraction with methanol, ethanol, iso-propanol, acetone, ethyl acetate, carbon dioxide (CO2), hexane, methylene chloride, chloroform or other solvents or solvent mixtures of comparable polarity. The extracts are characterized by the presence of active skin irritation-reducing amounts of constituents such as e.g. gingerols, shogaols, gingerdiols, dehydrogingerdiones and/or paradols.

Desquamating agents. The compositions may also contain desquamating agents (component b5) in amounts of about 0.1 to about 30% b.w. preferably about 0.5 to about 15% b.w., particularly preferably about 1 to about 10% b.w. based on the total weight of the preparation. The expression "desquamating agent" is understood to mean any compound capable of acting:

either directly on desquamation by promoting exfoliation, such as β-hydroxy acids, in particular salicylic acid and its derivatives (including 5-n-octanoylsalicylic acid); α-hydroxy acids, such as glycolic, citric, lactic, tartaric, malic or mandelic acids; urea; gentisic acid; oligofucoses; cinnamic acid; extract of Sophora japonica; resveratrol and some derivatives of jasmonic acid;

or on the enzymes involved in the desquamation or the degradation of the corneodesmosomes, glycosidases, stratum corneum chymotryptic enzyme (SCCE) or other proteases (trypsin, chymotrypsin-like). There may be mentioned agents chelating inorganic salts: EDTA; N-acyl-N,N',N'-ethylenediaminetriacetic acid; aminosulphonic compounds and in particular (N-2-hydroxyethylpiperazine-N-2-ethane)sulphonic acid (HEPES); derivatives of 2-oxothiazolidine-4-carboxylic acid (procysteine); derivatives of alpha-amino acids of the glycine type (as described in EP-0 852 949, and sodium methylglycine diacetate marketed by BASF under the trade name TRILON M); honey; sugar derivatives such as O-octanoyl-6-D-maltose and N-acetylglucosamine; chestnut extracts such as those marketed by the company SILAB under the name Recoverine®, prickly pear extracts such as those marketed under the name Exfolactive® by the company SILAB, or Phytosphingosine SLC® (phytosphingosine grafted with a salicylic acid) marketed by the company Degussa.

Desquamating agents suitable for the invention may be chosen in particular from the group comprising sulphonic acids, calcium chelators, a-hydroxy acids such as glycolic, citric, lactic, tartaric, malic or mandelic acids; ascorbic acid and its derivatives such as ascorbyl glucoside and magnesium ascorbyl phosphate; nicotinamide; urea; (N-2-hydroxyethylpiperazine-N-2-ethane)sulphonic acid (HEPES), β-hydroxy acids such as salicylic acid and its derivatives, retinoids such as retinol and its esters, retinal, retinoic acid and its derivatives, those described in the documents FR 2570377 A1, EP 0199636 A1, EP 0325540 A1, EP 0402072 A1, chestnut or prickly pear extracts, in particular marketed by SILAB; reducing compounds such as cysteine or cysteine precursors.

Desquamating agents which can be used are also nicotinic acid and its esters and nicotinamide, also called vitamin B3 or vitamin PP, and ascorbic acid and its precursors, as described in particular in application EP 1529522 A1.

Anti-cellulite agents. Anti-cellulite agents and lipolytic agents are preferably selected from the group consisting of those described in WO 2007/077541, and beta-adrenergic receptor agonists such as synephrine and its derivatives, and cyclohexyl carbamates described in WO 2010/097479. Agents enhancing or boosting the activity of anti-cellulite agents, in particular agents which stimulate and/or depolarise C nerve fibres, are preferably selected from the group consisting of capsaicin and derivatives thereof, vanillyl-nonylamid and derivatives thereof, L-carnitine, coenzym A, isoflavonoides, soy extracts, ananas extract and conjugated linoleic acid.

Fat enhancing agents. Formulations and products according to the present invention may also comprise one or more fat enhancing and/or adipogenic agents as well as agents enhancing or boosting the activity of fat enhancing agents. A fat enhancing agent is for example hydroxymethoxyphenyl propylmethylmethoxybenzofuran (trade name: Sym3D®).

Physiological Cooling Agents

The compositions may also contain one or more substances with a physiological cooling effect (cooling agents), which are preferably selected here from the following list: menthol and menthol derivatives (for example L-menthol, D-menthol, racemic menthol, isomenthol, neoisomenthol, neomenthol) menthylethers (for example (I-menthoxy)-1,2-propandiol, (1-menthoxy)-2-methyl-1,2-propandiol, 1-menthyl-methylether), menthone glyceryl acetal, menthone glyceryl ketal or mixtures of both, menthylesters (for example menthylformiate, menthylacetate, menthylisobutyrate, menthyhydroxyisobutyrat, menthyllactates, L-menthyl-L-lactate, L-menthyl-D-lactate, menthyl-(2-methoxy) acetate, menthyl-(2-methoxyethoxy)acetate, menthylpyroglutamate), menthylcarbonates (for example menthylpropyleneglycolcarbonate, menthylethyleneglycolcarbonate, menthylglycerolcarbonate or mixtures thereof), the semi-esters of menthols with a dicarboxylic acid or derivatives thereof (for example mono-menthylsuccinate, mono-menthylglutarate, mono-menthylmalonate, O-menthyl succinic acid ester-N,N-(dimethyl)amide, O-menthyl succinic acid ester amide), menthanecarboxylic acid amides (in this case preferably menthanecarboxylic acid-N-ethylamide [WS3] or N$^\alpha$-(menthanecarbonyl)glycinethylester [WS5], as described in U.S. Pat. No. 4,150,052, menthanecarboxylic acid-N-(4-cyanophenyl)amide or menthanecarboxylic acid-N-(4-cyanomethylphenyl)amide as described in WO 2005 049553 A1, menthanecarboxylic acid-N-(alkoxyalkyl)amides), menthone and menthone derivatives (for example L-menthone glycerol ketal), 2,3-dimethyl-2-(2-propyl)-butyric acid derivatives (for example 2,3-dimethyl-2-(2-propyl)-butyric acid-N-methylamide [WS23]), isopulegol or its esters (I-(−)-isopulegol, I-(−)-isopulegolacetate), menthane derivatives (for example p-menthane-3,8-diol), cubebol or synthetic or natural mixtures, containing cubebol, pyrrolidone derivatives of cycloalkyldione derivatives (for example 3-methyl-2(1-pyrrolidinyl)-2-cyclopentene-1-one) or tetrahydropyrimidine-2-one (for example iciline or related compounds, as described in WO 2004/026840), further carboxamides (for example N-(2-(pyridin-2-yl)ethyl)-3-p-menthanecarboxamide or related compounds), (1R,2S,5R)—N-(4-Methoxyphenyl)-5-methyl-2-(1-isopropyl)cyclohexane-carboxamide [WS12], oxamates (preferably those described in EP 2033688 A2) and [(1R,2S,5R)-2-isopropyl-5-methyl-cyclohexyl] 2-(ethylamino)-2-oxo-acetate (X Cool).

Anti-Inflammatory Agents

The compositions may also contain anti-inflammatory and/or redness and/or itch ameliorating ingredients, in particular steroidal substances of the corticosteroid type selected from the group consisting of hydrocortisone, dexamethasone, dexamethasone phosphate, methyl prednisolone or cortisone, are advantageously used as anti-inflammatory active ingredients or active ingredients to relieve reddening and itching, the list of which can be extended by the addition of other steroidal anti-inflammatories. Non-steroidal anti-inflammatories can also be used. Examples which can be cited here are oxicams such as piroxicam or tenoxicam; salicylates such as aspirin, disalcid, solprin or fendosal; acetic acid derivatives such as diclofenac, fenclofenac, indomethacin, sulindac, tolmetin or clindanac; fenamates such as mefenamic, meclofenamic, flufenamic or niflumic; propionic acid derivatives such as ibuprofen, naproxen, benoxaprofen or pyrazoles such as phenylbutazone, oxyphenylbutazone, febrazone or azapropazone. Anthranilic acid derivatives, in particular avenanthramides described in WO 2004 047833 A1, are preferred anti-itch ingredients in a composition according to the present invention.

Also useful are natural or naturally occurring anti-inflammatory mixtures of substances or mixtures of substances that alleviate reddening and/or itching, in particular extracts or fractions from camomile, Aloe vera, Commiphora species, Rubia species, willow, willow-herb, oats, calendula, arnica, St John's wort, honeysuckle, rosemary, Passiflora incarnata, witch hazel, ginger or Echinacea; preferably selected from the group consisting of extracts or fractions from camomile, Aloe vera, oats, calendula, arnica, honeysuckle, rosemary, witch hazel, ginger or Echinacea, and/or pure substances, preferably alpha-bisabolol, apigenin, apigenin-7-glucoside, gingerols, shogaols, gingerdiols, dehydrogingerdiones, paradols, natural or naturally occuring avenanthramides, preferably tranilast, avenanthramide A, avenanthramide B, avenanthramide C, non-natural or non-naturally occuring avenanthramides, preferably dihydroavenanthramide D, dihydroavenanthramide E, avenanthramide D, avenan-thramide E, avenanthramide F, boswellic acid, phytosterols, glycyrrhizin, glabridin and licochalcone A; preferably selected from the group consisting of alpha-bisabolol, natural avenanthramides, non-natural avenanthramides, preferably dihydroavenanthramide D (as described in WO 2004 047833 A1), boswellic acid, phytosterols, glycyrrhizin, and licochalcone A, and/or allantoin, panthenol, lanolin, (pseudo-)ceramides [preferably Ceramide 2, hydroxypropyl bispalmitamide MEA, cetyloxypropyl glyceryl methoxypropyl myristamide, N-(1-hexadecanoyl)-4-hydroxy-L-proline (1-hexadecyl) ester, hydroxyethyl palmityl oxyhydroxypropyl palmitamide], glycosphingolipids, phytosterols, chitosan, mannose, lactose and â-glucans, in particular 1,3-1,4-â-glucan from oats.

When bisabolol is used in the context of the present invention it can be of natural or synthetic origin, and is preferably "alpha-bisabolol". Preferably, the bisabolol used is synthetically prepared or natural (−)-alpha-bisabolol and/or synthetic mixed-isomer alpha-bisabolol. If natural (−)-alpha-bisabolol is used, this can also be employed as a constituent of an essential oil or of a plant extract or of a fraction thereof, for example as a constituent of (fractions of) oil or extracts of camomile or of *Vanillosmopsis* (in particular *Vanillosmopsis erythropappa* or *Vanillosmopsis arborea*). Synthetic alpha-bisabolol is obtainable, for example, under the name "Dragosantol" from Symrise.

Anti-Microbial Agents

Suitable anti-microbial agents are, in principle, all substances effective against Gram-positive bacteria, such as, for example, 4-hydroxybenzoic acid and its salts and esters, N-(4-chlorophenyl)-N'-(3,4-dichlorophenyl)urea, 2,4,4'-trichloro-2'-hydroxy-diphenyl ether (triclosan), 4-chloro-3,5-dimethyl-phenol, 2,2'-methylenebis(6-bromo-4-chlorophenol), 3-methyl-4-(1-methylethyl)phenol, 2-benzyl-4-chloro-phenol, 3-(4-chlorophenoxy)-1,2-propanediol, 3-iodo-2-propynyl butylcarbamate, chlorhexidine, 3,4,4'-trichlorocarbanilide (TTC), antibacterial fragrances, thymol, thyme oil, eugenol, oil of cloves, menthol, mint oil, farnesol, phenoxyethanol, glycerol monocaprate, glycerol monocaprylate, glycerol monolaurate (GML), diglycerol monocaprate (DMC), salicylic acid N-alkylamides, such as, for example, n-octylsalicylamide or n-decylsalicylamide.

Carriers and Hydrotropes

Preferred cosmetics carrier materials are solid or liquid at 25° C. and 1013 mbar (including highly viscous substances) as for example glycerol, 1,2-propylene glycol, 1,2-butylene glycol, 1,3-propylene glycol, 1,3-butylene glycol, ethanol, water and mixtures of two or more of said liquid carrier materials with water. Optionally, these preparations according to the invention may be produced using preservatives or solubilizers. Other preferred liquid carrier substances, which may be a component of a preparation according to the invention are selected from the group consisting of oils such as vegetable oil, neutral oil and mineral oil.

Preferred solid carrier materials, which may be a component of a preparation according to the invention are hydrocolloids, such as starches, degraded starches, chemically or physically modified starches, dextrins, (powdery) maltodextrins (preferably with a dextrose equivalent value of 5 to 25, preferably of 10-20), lactose, silicon dioxide, glucose, modified celluloses, gum arabic, ghatti gum, traganth, karaya, carrageenan, pullulan, curdlan, xanthan gum, gellan gum, guar flour, carob bean flour, alginates, agar, pectin and inulin and mixtures of two or more of these solids, in particular maltodextrins (preferably with a dextrose equivalent value of 15-20), lactose, silicon dioxide and/or glucose.

In addition, hydrotropes, for example ethanol, isopropyl alcohol or polyols, may be used to improve flow behaviour. Suitable polyols preferably contain 2 to 15 carbon atoms and at least two hydroxyl groups. The polyols may contain other functional groups, more especially amino groups, or may be modified with nitrogen. Typical examples are glycerol;

alkylene glycols such as, for example, ethylene glycol, diethylene glycol, propylene glycol, butylene glycol, hexylene glycol and polyethylene glycols with an average molecular weight of 100 to 1000 Dalton;

technical oligoglycerol mixtures with a degree of self-condensation of 1.5 to 10, such as for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

amino sugars, for example glucamine;

dialcoholamines, such as diethanolamine or 2-aminopropane-1,3-diol.

Preservatives

Suitable preservatives are, for example, phenoxyethanol, formaldehyde solution, parabens, pentanediol or sorbic acid and the other classes of compounds listed in Appendix 6, Parts A and B of the Kosmetikverordnung ("Cosmetics Directive").

Perfume Oils and Fragrances

Suitable perfume oils are mixtures of natural and synthetic perfumes. Natural perfumes include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamom, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxy-citronellal, lilial and bourgeonal. Examples of suitable ketones are the ionones, ⍺-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable perfume. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, ladanum oil and lavendin oil. The following are preferably used either individually or in the form of mixtures: bergamot oil, dihydromyrcenol, lilial, lyral, citronellol, phenylethyl alcohol, hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Dyes

Suitable dyes are any of the substances suitable and approved for cosmetic purposes as listed, for example, in the publication "Kosmetische Färbemittel" of the Farbstoffkommission der Deutschen Forschungsgemeinschaft, Verlag Chemie, Weinheim, 1984, pages 81 to 106. Examples include cochineal red A (C.I. 16255), patent blue V (C.I. 42051), indigotin (C.I. 73015), chlorophyllin (C.I. 75810), quinoline yellow (C.I. 47005), titanium dioxide (C.I. 77891), indanthrene blue RS (C.I. 69800) and madder lake (C.I. 58000). Luminol may also be present as a luminescent dye. Advantageous coloured pigments are for example titanium dioxide, mica, iron oxides (e.g. $Fe_2O_3$ $Fe_3O_4$, FeO(OH)) and/or tin oxide. Advantageous dyes are for example carmine, Berlin blue, chromium oxide green, ultramarine blue and/or manganese violet.

Preparations

Preferred compositions according to the present inventions are selected from the group of products for treatment, protecting, care and cleansing of the skin and/or hair or as a make-up product, preferably as a leave-on product (meaning that the one or more compounds of formula (I) stay on the skin and/or hair for a longer period of time, compared to rinse-off products, so that the moisturizing and/or anti-ageing and/or wound healing promoting action thereof is more pronounced).

The formulations according to the invention are preferably in the form of an emulsion, e.g. W/O (water-in-oil), O/W (oil-in-water), W/O/W (water-in-oil-in-water), O/W/O (oil-in-water-in-oil) emulsion, PIT emulsion, Pickering emulsion, emulsion with a low oil content, micro- or nanoemulsion, a solution, e.g. in oil (fatty oils or fatty acid esters, in particular $C_6$-$C_{32}$ fatty acid $C_2$-$C_{30}$ esters) or silicone oil, dispersion, suspension, creme, lotion or milk, depending on the production method and ingredients, a gel (including hydrogel, hydrodispersion gel, oleogel), spray (e.g. pump spray or spray with propellant) or a foam or an impregnating solution for cosmetic wipes, a detergent, e.g. soap, synthetic detergent, liquid washing, shower and bath preparation, bath product (capsule, oil, tablet, salt, bath salt, soap, etc.), effervescent preparation, a skin care product such as e.g. an emulsion (as described above), ointment, paste, gel (as described above), oil, balsam, serum, powder (e.g. face powder, body powder), a mask, a pencil, stick, roll-on, pump, aerosol (foaming, non-foaming or post-foaming), a deodorant and/or antiperspirant, mouthwash and mouth rinse, a foot care product (including keratolytic, deodorant), an insect repellent, a sunscreen, aftersun preparation, a shaving product, aftershave balm, pre- and aftershave lotion, a depilatory agent, a hair care product such as e.g. shampoo (including 2-in-1 shampoo, antidandruff shampoo, baby shampoo, shampoo for dry scalps, concentrated shampoo), conditioner, hair tonic, hair water, hair rinse, styling creme, pomade, perm and setting lotion, hair spray, styling aid (e.g. gel or wax), hair smoothing agent (detangling agent, relaxer), hair dye such as e.g. temporary direct-dyeing hair dye, semi-permanent hair dye, permanent hair dye, hair conditioner, hair mousse, eye care product, make-up, make-up remover or baby product.

The formulations according to the invention are particularly preferably in the form of an emulsion, in particular in the form of a W/O, O/W, W/O/W, O/W/O emulsion, PIT emulsion, Pickering emulsion, emulsion with a low oil content, micro- or nanoemulsion, a gel (including hydrogel, hydrodispersion gel, oleogel), a solution e.g. in oil (fatty oils or fatty acid esters, in particular $C_6$-$C_{32}$ fatty acid $C_2$-$C_{30}$ esters)) or silicone oil, or a spray (e.g. pump spray or spray with propellant).

Auxiliary substances and additives can be included in quantities of 5 to 99% b.w., preferably 10 to 80% b.w., based on the total weight of the formulation. The amounts of cosmetic or dermatological auxiliary agents and additives and perfume to be used in each case can easily be determined by the person skilled in the art by simple trial and error, depending on the nature of the particular product.

The preparations can also contain water in a quantity of up to 99% b.w., preferably 5 to 80% b.w., based on the total weight of the preparation.

Oral Compositions

Another object of the present invention relates to oral compositions comprising the blend of TRPV1/TRPV3 modulators and alkandiols as explained above, preferably in an amount suitable to effect warming sensation on human skin or mucous membranes, such as for example amounts of from 0.01 to about 5% b.w., preferably 0.1 to 2% b.w. and more preferred about 0.2 to about 1% b.w.—calculated on the final composition.

Typical examples for suitable oral compositions encompass (hard boiled) candies, compressed tablets, chewing gums, toothpastes and mouth washes. The manufacture and composition of said oral compositions are described as follows:

Candies

According to the present invention the preferred candies are so-called hard-boiled candies. Their bases are usually prepared from a mixture of sugar and other carbohydrates that are kept in an amorphous or glassy condition. This form can be considered a solid syrup of sugars generally having up to about 4.5% b.w. moisture, based on the weight of the candy base, with about 0.5 to about 2.5% b.w. being preferred and about 1.0 to about 1.5% b.w. being most preferred. Such materials normally contain up to 65% b.w. corn syrup, up to 80% b.w. sugar and from 0.1 to 5.0% b.w. water. Generally, the ratio of sugar (or other sweetener suitable for candy formulation) to corn syrup is within the range of about 70:25 to about 45:55 with about 60:40 being preferred. The syrup component generally is prepared from corn syrups high in fructose, but may include other materials. Further ingredients such as flavourings, sweeteners, acidulents, colorants and so forth may also be added.

Hard boiled candy bases may also be prepared from non-fermentable sugars such as sorbitol, mannitol, xylitol, maltitol, hydrogenated starch hydrolysate, hydrogenated corn syrup and mixtures thereof. The candy bases may contain up to about 95% sorbitol, a mixture of sorbitol and mannitol at a ratio of about 9.5 to 0.5 up to about 7.5 to 2.5 and hydrogenated corn syrup up to about 55% of the syrup component.

Compressed Tablets

According to the present invention the oral compositions can represent compressed tablets, comprising the liquid flavour in amounts of typically about 0.1 to about 0.6% b.w. and preferably about 0.5% b.w.

Chewing Gums

Chewing gums typically consist of a water-insoluble vase component, a water-soluble component and additives providing for example a specific flavour.

The water-insoluble base, which is also known as the "gum base", typically comprises natural or synthetic elastomers, resins, fats and oils, plasticizers, fillers, softeners, dyes and optionally waxes. The base normally makes up 5 to 95% by weight, preferably 10 to 50% by weight and more particularly 20 to 35% by weight of the composition as a whole. In one typical embodiment of the invention, the base consists of 20 to 60% by weight synthetic elastomers, 0 to 30% by weight natural elastomers, 5 to 55% by weight plasticizers, 4 to 35% by weight fillers, 5 to 35% by weight softeners and small amounts of additives, such as dyes, antioxidants and the like, with the proviso that they are soluble in water at best in small quantities.

Suitable synthetic elastomers are, for example, polyisobutylenes with average molecular weights (as measured by GPC) of 10,000 to 100,000 and preferably 50,000 to 80,000, isobutylene/isoprene copolymers ("butyl elastomers"), styrene/butadiene copolymers (styrene:butadiene ratio, for example, 1:3 to 3:1). polyvinyl acetates with average molecular weights (as measured by GPC) of 2,000 to 90,000 and preferably 10,000 to 65,000, polyisoprenes, poly-ethylenes, vinyl acetate/vinyl laurate copolymers and mixtures thereof. Examples of suitable natural elastomers are rubbers, such as for example smoked or liquid latex or guayuls, and natural gums, such as jelutong, lechi caspi, perillo, sorva, massaranduba balata, massaranduba chocolate, nispero, rosindinba, chicle, gutta hang kang and mixtures thereof. The choice of the synthetic and natural elastomers and their mixing ratios essentially depends on whether or not bubbles are to be produced with the chewing gums (bubble gums). Elastomer mixtures containing jelutong, chicle, sorva and massaranduba are preferably used.

In most cases, the elastomers are too hard or lack plasticity for satisfactory processing, so that it has been found to be of advantage to use special plasticizers which, of course, must also satisfy in particular all requirements relating to acceptability as food additives. In this respect, suitable plasticizers are, above all, esters of resin acids, for example esters of lower aliphatic alcohols or polyols with completely or partly hydrogenated, monomeric or oligomeric resin acids. In particular, the methyl, glycerol or pentaerythritol esters or mixtures thereof are used for this purpose. Alternatively, terpene resins, which may be derived from .alpha.-pinene, .beta.-pinene, .delta.-limonene or mixtures thereof, could also be used.

Suitable fillers or texturizers are magnesium or calcium carbonate, ground pumice stone, silicates, especially magnesium or aluminium silicates, clays, aluminium oxides, talcum, titanium dioxide, mono-, di- and tricalcium phosphate and cellulose polymers.

Suitable softeners or emulsifiers are tallow, hydrogenated tallow, hydrogenated or partly hydrogenated vegetable oils, cocoa butter, partial glycerides, lecithin, triacetin and saturated or unsaturated fatty acids containing 6 to 22 and preferably 12 to 18 carbon atoms and mixtures thereof.

Suitable dyes and whiteners are, for example, the FD&C types, plant and fruit extracts permitted for colouring foods and titanium dioxide. The gum bases may also contain waxes or may be wax-free In addition to the water-insoluble gum base, chewing gum preparations regularly contain a water-soluble component which is formed, for example, by softeners, sweeteners, fillers, flavours, flavour enhancers, emulsifiers, dyes, acidifiers, antioxidants and the like, with the proviso that the constituents have at least adequate solubility in water. Accordingly, individual constituents may belong both to the water-insoluble phase and to the water-soluble phase, depending on the water solubility of the special representatives. However, combinations may also be used, for example a combination of a water-soluble and a water-insoluble emulsifier, in which case the individual representatives are present in different phases. The water-insoluble component usually makes up 5 to 95% by weight and preferably 20 to 80% by weight of the preparation.

Water-soluble softeners or plasticizers are added to the chewing gum compositions to improve chewability and the chewing feel and are present in the mixtures in quantities of typically 0.5 to 15% by weight. Typical examples are glycerol, lecithin and aqueous solutions of sorbitol, hydrogenated starch hydrolysates or corn sirup.

Fillers are particularly suitable for the production of low-calorie chewing gums and may be selected, for example, from polydextrose, raftilose, raftilin, fructo-oligosaccharides (NutraFlora), palatinose oligosaccharides, guar gum hydrolyzates (Sun Fiber) and dextrins.

The chewing gums may additionally contain auxiliaries and additives which are suitable, for example, for dental care, more particularly for controlling plaque and gingivitis, such as for example chlorhexidine, CPC or triclosan. They may also contain pH adjusters (for example buffer or urea), anti-caries agents (for example phosphates or fluorides), biogenic agents (antibodies, enzymes, caffeine, plant extracts), providing these substances are permitted in foods and do not undesirably interact with one another.

Toothpastes and Mouth Washes

Toothpastes or tooth creams are generally understood to be paste-like preparations of water, thickeners, humectants, abrasives or polishes, surfactants, sweeteners, flavorings, deodorizing agents and agents active against oral and dental diseases. In toothpastes according to the invention, any of the usual polishes may be used, such as chalk, dicalcium phosphate, insoluble sodium metaphosphate, aluminium silicates, calcium pyrophosphate, finely particulate synthetic resins, silicas, aluminium oxide and aluminium oxide trihydrate. Particularly suitable polishes for toothpastes according to the invention are finely particulate xerogel silicas, hydrogel silicas, precipitated silicas, aluminium oxide trihydrate and finely particulate.alpha.-alumina, or mixtures of these polishes. Such polishes are preferably used in quantities of from about 15 to 40% by weight of the toothpaste. Preferred humectants used for toothpastes according to the invention include low molecular weight polyethylene glycols, glycerol, sorbitol or mixtures thereof in quantities of up to about 50% by weight of the toothpaste. Among the known thickeners for use with toothpastes according to the invention, particularly preferred are the thickening, finely particulate gel silicas and nonionic hydrocolloids, such as hydroxy ethyl cellulose, hydroxy propyl guar, hydroxy ethyl starch, polyvinyl pyrrolidone, high molecular weight polyethylene glycol and vegetable gums, such as tragacanth, agaragar, carrageen moss, gum arabic and xanthan gum. The desired flavor and aroma for preparations in accordance with the invention may be obtained by adding the components (a) and/or (b) and optionally also (c). It is also advantageous adding caries inhibitors to the oral preparations in the form of, for example, alkali fluorides, alkali monofluorophosphates or alkali salts of organophosphonic acids. In addition, the oral preparations according to the invention may contain other standard auxiliaries, such as dyes, preservatives and opacifiers, for example titanium dioxide. For mouthwashes, the oral compositions according to the invention may readily be combined with aqueous-alcoholic solutions containing different amounts of ethereal oils, emulsifiers, astringent and toning drug extracts, caries-inhibiting additives and flavour correctants.

Additives

The oral compositions of the present invention may include additional additives as for examples sweeteners or vitamins, in amounts of from about 0.1 to about 10% b.w. These additives may also represent components of the respective medicaments.

Sweeteners

Suitable sweet-tasting substances, including natural sources of these substances (component e5), such as for example sweet-tasting carbohydrates or sugars (e.g. sucrose (synonymous with saccharose), trehalose, lactose, maltose, melizitose, raffinose, palatinose, lactulose, D-fructose, D-glucose, D-galactose, L-rhamnose, D-sorbose, D-mannose, D-tagatose, D-arabinose, L-arabinose, D-ribose, D-glyceraldehyde, maltodextrin) or vegetable preparations containing predominantly these carbohydrates (e.g. from sugar beet (*Beta vulgaris* ssp., sugar fractions, sugar syrup, molasses), from sugar cane (*Saccharum officinarum* ssp., e.g. molasses, sugar syrups), from sugar maple (*Acer* ssp.), from agave (agave thick juice), synthetic/enzymatic hydrolysates of starch or sucrose (e.g. invert sugar syrup, highly enriched fructose syrups made from corn starch), fruit concentrates (e.g. from apples or pears, apple syrup, pear syrup), sugar alcohols (e.g. erythritol, threitol, arabitol, ribitol, xylitol, sorbitol, mannitol, dulcitol, lactitol), proteins (e.g. miraculin, monellin, thaumatin, curculin, brazzein), sweeteners (magap, sodiumcyclamate, acesulfame K, neohesperidin dihydrochalcone, saccharin sodium salt, Aspartame®, superaspartame, neotame, alitame, sucralose, stevioside, rebaudioside, lugduname, carrelame, sucronate, sucrooctate, monatin, phyllodulcin), certain sweet-tasting amino acids (glycine, D-leucine, D-threonine, D-asparagine, D-phenylalanine, D-tryptophan, L-proline), other sweet-tasting low-molecular substances (e.g. hernandulcin, dihydrochalcone glycosides, glycyrrhizin, glycyrrhetinic acid ammonium salt or other glycyrrhetinic acid derivatives), liquorice extracts (*Glycyrrhizza glabra* ssp.), Lippia dulcis extracts, *Momordica* ssp. extracts or individual substances (in particular *Momordica grosvenori* [Luo Han Guo] and the mogrosides obtained therefrom), *Hydrangea dulcis* or *Stevia* ssp. (e.g. *Stevia rebaudiana*) extracts or individual substances.

Vitamins

In another embodiment of the present invention the compositions may include vitamins (component e1). Vitamins have diverse biochemical functions. Some have hormone-like functions as regulators of mineral metabolism (e.g., vitamin D), or regulators of cell and tissue growth and differentiation (e.g., some forms of vitamin A). Others function as antioxidants (e.g., vitamin E and sometimes vitamin C). The largest numbers of vitamins (e.g. B complex vitamins) act as precursors for enzyme cofactors that help enzymes in their work as catalysts in metabolism. In this role, vitamins may be tightly bound to enzymes as part of prosthetic groups: For example, biotin is part of enzymes involved in making fatty acids. Vitamins may also be less tightly bound to enzyme catalysts as coenzymes, detachable molecules that function to carry chemical groups or electrons between molecules. For example, folic acid carries various forms of carbon group—methyl, formyl, and methylene—in the cell. Although these roles in assisting enzyme-substrate reactions are vitamins' best-known function, the other vitamin functions are equally important. In the course of the present invention suitable vitamins are selected from the group consisting of Vitamin A (retinol, retinal, beta carotene),
Vitamin $B_1$ (thiamine),
Vitamin $B_2$ (riboflavin),
Vitamin $B_3$ (niacin, niacinamide),
Vitamin $B_5$ (panthothenic acid),
Vitamin $B_6$ (pyridoxine, pyridoxamine, paridoxal),
Vitamin $B_7$ (biotin),
Vitamin $B_9$ (folic acid, folinic acid),
Vitamin $B_{12}$ (cyanobalamin, hydoxycobalmin, methylcobalmin),
Vitamin C (ascorbic acid),
Vitamin D (cholecalciferol),
Vitamin E (tocopherols, tocotrienols), and
Vitamin K (phyolloquinone, menaquinone).

The preferred vitamins are ascorbic acid and tocopherols. Said vitamins may be present in the food composition in amounts of about 0.1 to about 5% b.w., and preferably about 0.5 to about 1% b.w.

INDUSTRIAL APPLICATION

Another object of the present invention is related to a method for improving warming sensation and/or dermatological compatibility of TRPV1 and/or TRPV3 modulators, comprising the following steps (a) providing at least one TRPV1 and/or TRPV3 modulator;
(b) blending said at least one TRPV1 and/or TRPV3 modulator with at least one 1,2 alkandiol having 5 to 12 carbon atoms;
(c) optionally incorporating the blend of step (b) into a cosmetic formulation, and
(d) applying either the blend of step (b) or the formulation of step (c) on human skin or mucous membranes.

Another object of the present invention encompasses the use of a composition comprising or consisting of (a) at least one TRPV1 and/or TRPV3 modulator and
(b) at least one 1,2-alkandiol having 5 to 12 carbon atoms for simultaneously improving warming sensation and dermatological compatibility on human skin and mucous membranes.

Finally, the present invention also relates to the use of 1,2-alkandiols having 6 to 12 carbon atoms for simultaneously improving warming sensation and dermatological compatibility of TRPV1 and/or TRPV3 modulators when applied to human skin or mucous membranes.

It should be noted that as far preferred species and preferred ranges are concerned the selections explained above are also valid for said method and said uses. A repetition is thus not necessary. In the following the invention is illustrated—but not limited—by several working and formulation examples.

EXAMPLES

Examples 1 and 2, Comparative Examples C1 and C2 Panel Text 1

Determination of warming sensation was conducted by a panel consisting of 16 untrained volunteers. Samples of 0.2 g of a standard cream formulation were placed on the forearm of each volunteer (about 55 cm$^2$, 50 rotations) for 20 minutes. Sensation was evaluated by using the following scale: (−1)=fresh; (0)=no sensation; (1)=slightly warm; (2)=warm; (3)=very warm; (4)=burning. The results are compiled in Table 1. All data represent average values. Δ stands for the standard deviation.

Examples 1 and 2 are according to the invention and refer to cream compositions comprising 0.4% b.w. vanillyl butyl ether (VBE)+0.8% b.w. 1,2-octandiol (Hydrolite® 8) and 0.4% b.w. vanillyl butyl ether and 0.6% b.w. 1,2-hexandiol/1,2-octandiol (1:1) (SymDiol® 68) respectively.

Comparative Examples C1 and C2 refer to a first placebo composition without warming agents and a second composition comprising 0.4% vanillyl butyl ether, but no alkandiols.

TABLE 1

Warming sensation

| Time [min] | C1 Average | Δ | C2 Average | Δ | 1 Average | Δ | 2 Average | Δ |
|---|---|---|---|---|---|---|---|---|
| 0.5 | −0.938 | 0.250 | −0.800 | 0.561 | −0.938 | 0.250 | −0.813 | 0.403 |
| 2 | −0.813 | 0.403 | −0.333 | 0.816 | −0.438 | 0.964 | −0.375 | 0.806 |
| 5 | −0.143 | 0.403 | 0.733 | 1.033 | 1.714 | 1.223 | 1.063 | 1.124 |
| 10 | −0.063 | 0.250 | 1.933 | 1.223 | 2.031 | 0.865 | 2.219 | 1.080 |
| 15 | −0.063 | 0.250 | 1.733 | 1.163 | 1.938 | 0.873 | 1.938 | 0.929 |
| 20 | 0.000 | 0.365 | 1.433 | 0.990 | 1.500 | 0.730 | 1.438 | 0.814 |

As one can derive from Table 1, adding alkandiols to vanillyl butyl ether leads to improved warming sensation over the full time set of 20 minutes. FIG. 1 shows the results once again as warming sensation versus time.

Examples 3 and 4, Comparative Examples C3 and C4
Panel Test 2

The panel test explained above was repeated with another standard cream formulation. The results are compiled in Table 2. All data represent average values.

Examples 3 and 4 are according to the invention and refer to cream compositions comprising 0.4% b.w. vanillyl butyl ether (VBE)+0.6% b.w. 1,2-octandiol (Hydrolite® 8) and 0.4% b.w. vanillyl butyl ether and 0.6% b.w. 1,2-hexandiol/1,2-octandiol (1:1) (SymDiol® 68) respectively.

Comparative Examples C3 and C4 refer to a first placebo composition without warming agents and a second composition comprising 0.4% vanillyl butyl ether, but no alkandiols.

TABLE 2

Warming sensation

| Time [min] | C3 Average | Δ | C4 Average | Δ | 3 Average | Δ | 4 Average | Δ |
|---|---|---|---|---|---|---|---|---|
| 0.5 | −0.882 | 0.332 | −0.824 | 0.529 | −1.000 | 0.000 | −0.882 | 0.332 |
| 2 | −0.765 | 0.437 | −0.471 | 0.717 | 0.059 | 1.298 | −0.765 | 0.437 |
| 5 | 0.000 | 0.500 | 0.971 | 1.256 | 2.313 | 1.105 | 1.647 | 1.367 |
| 10 | 0.000 | 0.000 | 1.971 | 1.205 | 2.765 | 1.033 | 2.353 | 1.272 |
| 15 | 0.118 | 0.485 | 1.853 | 1.057 | 2.059 | 0.966 | 2.118 | 0.993 |
| 20 | 0.059 | 0.243 | 1.588 | 1.176 | 1.882 | 1.269 | 1.647 | 0.996 |

Figure 2:
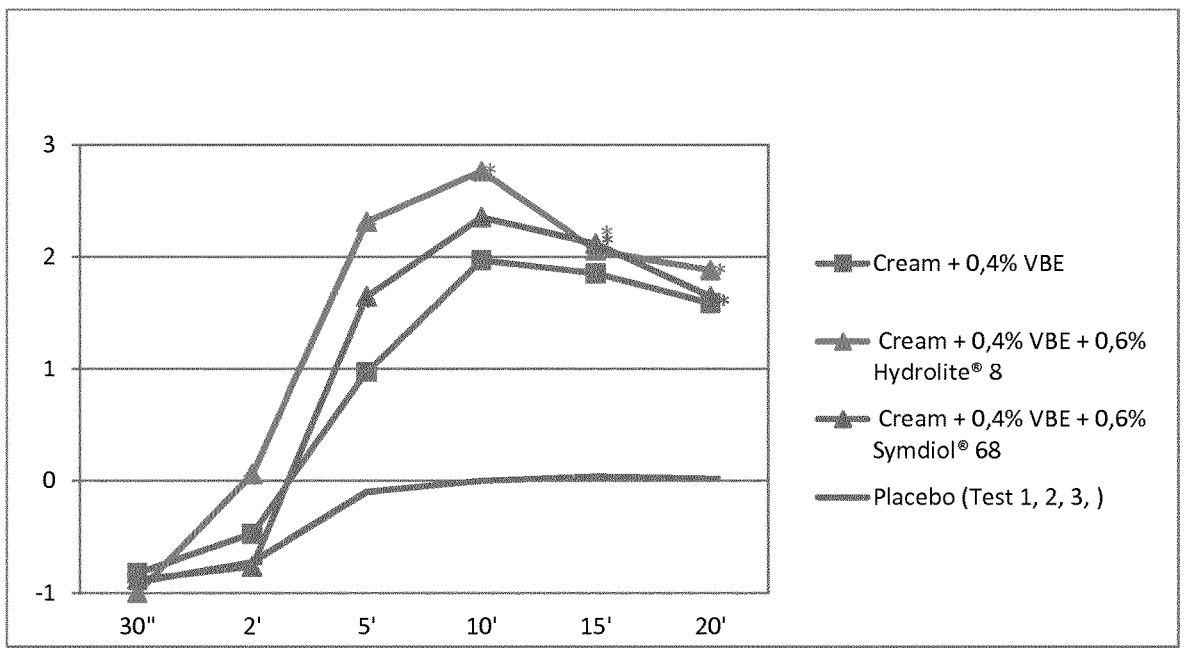

As one can derive from Table 2, adding alkandiols to vanillyl butyl ether again leads to improved warming sensation over the full time set of 20 minutes. FIG. 2 shows the results once again as warming sensation versus time.

Examples 5 to 8, Comparative Examples C5 to C8

Along with the evaluation of warming sensation the panellists voted whether the samples lead to unwanted side-effects, like burning, itching and the like. The compositions correspond to those indicated in the aforementioned examples. The results are depicted in Table 3. Provided is the percentage of panellists who indicated said negative effects on their skin.

TABLE 3

Negative side-effects on skin

| Time [min] | C1 | C2 | 1 | 2 | C3 | C4 | 3 | 4 |
|---|---|---|---|---|---|---|---|---|
| 0.5 | 0 | 0 | 0 | 0 | 6 | 0 | 0 | 0 |
| 2 | 0 | 0 | 0 | 0 | 6 | 6 | 0 | 0 |
| 5 | 0 | 6 | 6 | 6 | 6 | 6 | 6 | 6 |
| 10 | 0 | 20 | 20 | 13 | 6 | 18 | 16 | 16 |
| 15 | 0 | 33 | 25 | 13 | 0 | 24 | 21 | 21 |
| 20 | 0 | 27 | 13 | 19 | 0 | 29 | 25 | 18 |

Figure 3:
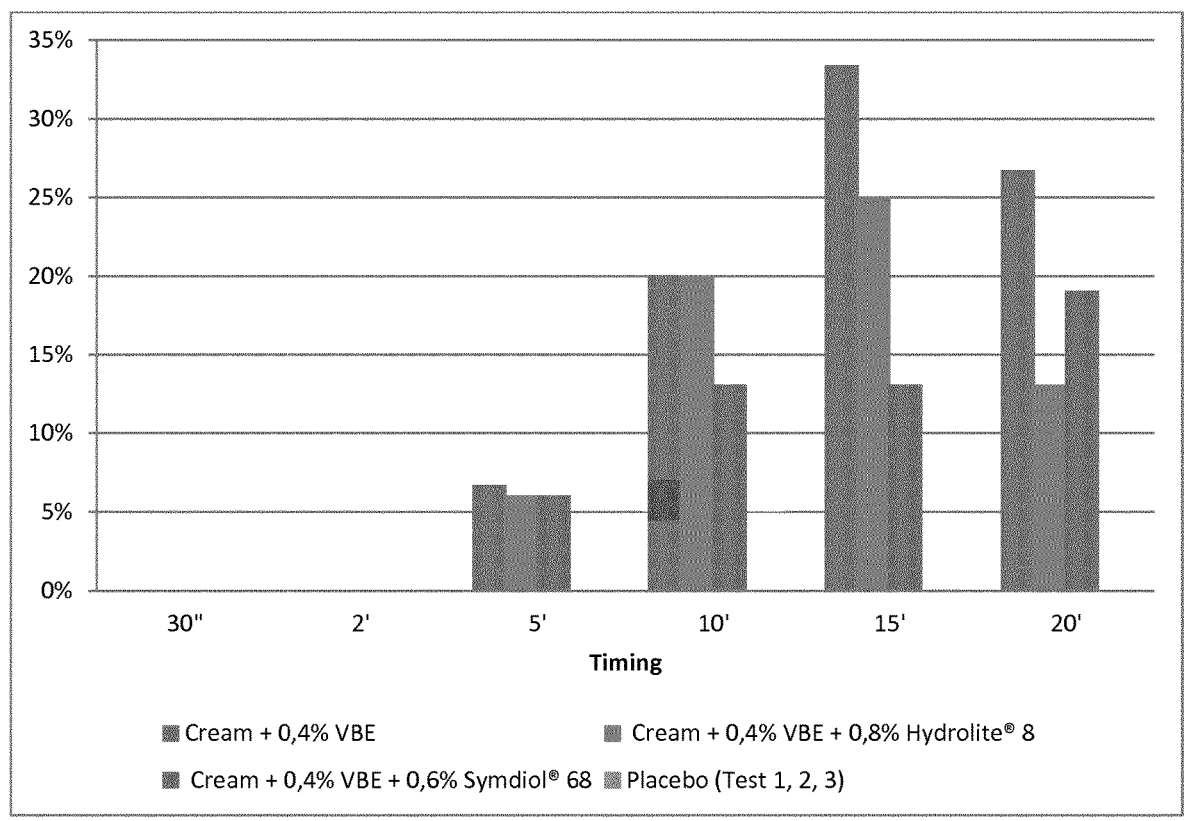
Figure 4:
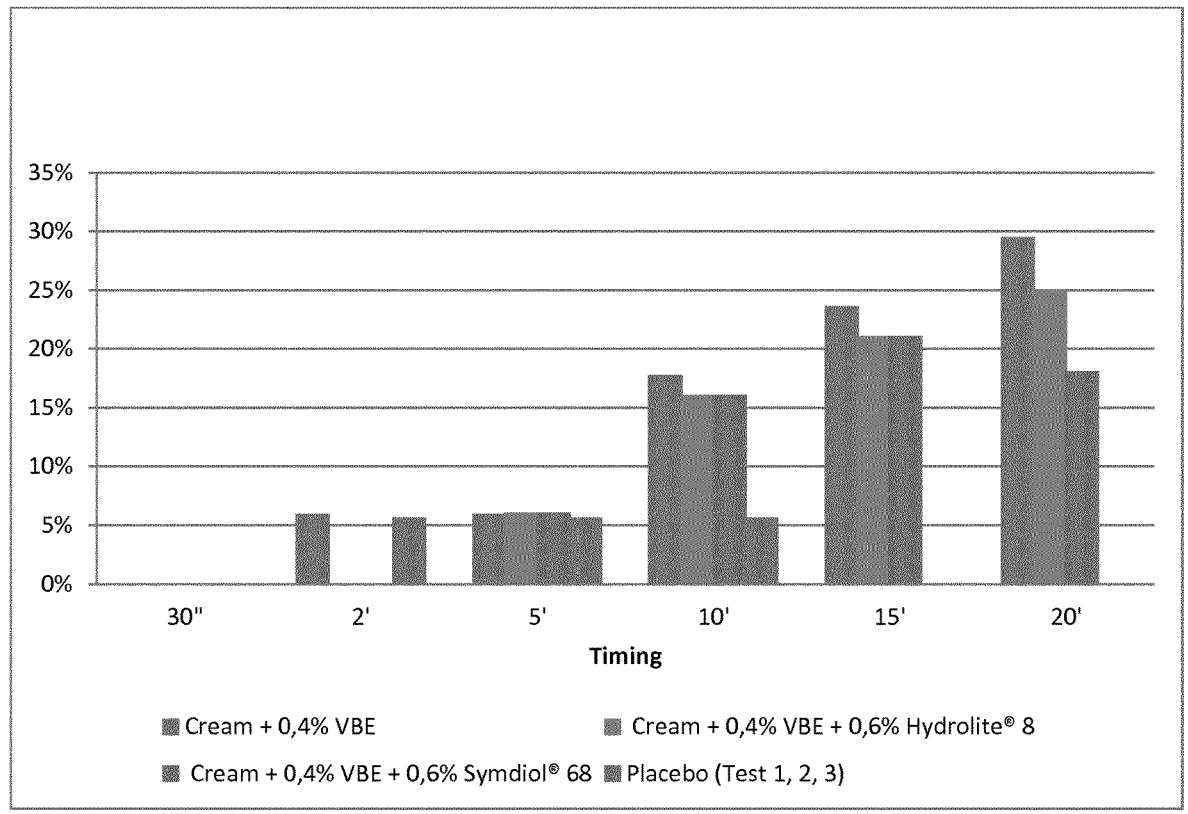

As one can see, adding 1,2-alkandiols to VEB leads to a significant reduction in negative side effects. The results are also shown in FIGS. 3 and 4.

TREK Receptor Screening

The human TREK-1 receptor is a temperature sensitive, mechano-gated potassium channels, present in human skin and neuronal cells. It is known to be involved in the signaling of temperature sensation. Here it cooperates with other ion channels in the relevant cell types. Literature indicated that a blockade of the TREK-1 receptor would lead to a better efficacy of TRP-channel activation.

To screen for TREK-1 receptor channel blockers, frog oocyte were transfected to transiently overexpress the human TREK-1 receptor. A substance database was screened on the cells. Read out was TREK-1medited currents, detected by manual patch clamp. The results are presented in the following Table 4.

TABLE 4

Blockade of TREK-1 receptor at 1 mMol

| Compound | F.I. | S.E.M. | Numbers of tests |
|---|---|---|---|
| None | 1.000 | | |
| Control (Fluoxetine) | 0.679 | 0.042 | 3 |
| 1,2-Dodecandiol | 0.733 | 0.027 | 4 |
| 1,2-Decandiol | 0.773 | 0.014 | 3 |
| 1,2-Octandiol | 0.855 | 0.014 | 3 |
| 1,2-Hexandiol | 0.942 | 0.022 | 3 |

The results clearly indicate that 1,2 alkandiols are able to inhibit the TREK-1 mediated current in the range of the positive control (fluoxetine).

FORMULATION EXAMPLES

The present invention is further illustrated by the following examples.

TABLE 5

O/W lotion (Amounts in % b.w.)

| Ingredients | Amount |
|---|---|
| Paraffin oil | 5.00 |
| Isopropyl palmitate | 5.00 |

TABLE 5-continued

O/W lotion (Amounts in % b.w.)

| Ingredients | Amount |
|---|---|
| Cetyl alcohol | 2.00 |
| Beeswax | 2.00 |
| Ceteareth-20 | 2.00 |
| PEG-20-glyceryl stearate | 1.50 |
| Glycerol | 3.00 |
| Perfume oil | 0.30 |
| Methylparaben | 0.30 |
| Vanillyl butyl ether | 0.30 |
| 1,2-octandiol | 0.30 |
| Water | ad 100.00 |

TABLE 6

Body lotion (Amounts in % b.w.)

| Ingredients | Amount |
|---|---|
| Cetearyl Alcohol | 2.00 |
| Ethylhexyl Isononanoate | 5.00 |
| Cetearyl Ethylhexanoate. Isopropyl Myristate | 3.00 |
| Glyceryl Oleate Citrate. Caprylic/Capric Triglyceride | 4.00 |
| Water (Aqua) | 79.50 |
| Carbomer | 0.30 |
| Sodium Benzoate | 0.100 |
| Propylene Glycol | 5.00 |
| Sodium Hydroxide 30% solution | 0.30 |
| Perfume oil | 0.30 |
| Triethylene Glycol. Imidazolidinyl Urea. Methylparaben. Propylparaben. Dehydroacetic Acid | 0.30 |
| Vanillyl butyl ether | 0.10 |
| 1,2-octandiol | 0.10 |

TABLE 7

Cream (Amounts in % b.w.)

| Ingredients | Amount |
|---|---|
| Paraffin oil | 10.00 |
| Ozokerite | 4.00 |
| Vaseline | 4.00 |

TABLE 7-continued

Cream (Amounts in % b.w.)

| Ingredients | Amount |
|---|---|
| Vegetable oil | 10.00 |
| Wool wax alcohol | 2.00 |
| Aluminium stearate | 0.40 |
| Perfume oil P1. P2. P3 or P4 | 0.70 |
| 1.2-pentanediol | 2.00 |
| Phenoxyethanol | 0.50 |
| Vanillyl butyl ether | 0.25 |
| 1,2-octandiol | 0.25 |
| Water | ad 100.00 |

TABLE 8

Cream (Amounts in % b.w.)

| Ingredients | INCI | Amount |
|---|---|---|
| Dracorin ® CE | Glyceryl Stearate Citrate | 1.00 |
| Lanette ® O | Cetearyl Alcohol | 2.00 |
| Cutina ® GMS-V | Glyceryl Stearate | 1.00 |
| Tegosoft ® MM | Myristyl Myristate | 1.00 |
| Xiameter ® PMX-0246. Cyclosiloxane | Cyclohexasiloxane (and) Cyclopentasiloxane | 0.50 |
| Dragoxat ® 89 | Ethylhexyl Isononanoate | 2.00 |
| PCL-Liquid 100 | Cetearyl Ethylhexanoate | 4.00 |
| Neutral Oil | Caprylic/Capric Triglyceride | 4.00 |
| Carbopol ® Ultrez 21 | Acrylates/C10-30 Alkyl Acrylate Crosspolymer | 0.20 |
| Keltrol ® CG-T | Xanthan Gum | 0.10 |
| Water | Water (Aqua) | Ad 100 |
| Glycerol 99.5 P. | Glycerol | 3.00 |
| Propylene Glycol -1.2 99 P GC | Propylene Glycol | 2.00 |
| Sodium Benzoate | Sodium Benzoate | 0.10 |
| Sodium Hydroxide 10% solution | Sodium Hydroxide | 0.50 |
| Perfume oil | Perfume | 0.30 |
| Euxyl ® K702 | Dehydroacetic Acid. Benzoic Acid. Phenoxyethanol.Polyaminopropyl Biguanide. Ethylhexylglycerin Vanillyl pentyl ether | 0.30 0.35 |
| SymDiol ® 68 | 1,2-hexandiol and 1,2-octandiol | 0.35 |

TABLE 9

Gel cream for feet (Amounts in % b.w.)

| Phase | Ingredients | INCI | Amount |
|---|---|---|---|
| A | Water | Aqua | Ad 100 |
| | Extrapone Lemongras | Propylene Glycol, Water, PEG-40 Hydrogenated Castor Oil, Trdeceth-9, *Cymbopogon Flexuosus* Leaf Oil, Lactic Acid | 0.50 |
| | Glycerol | Glycerol | 3.00 |
| | Symdiol ® 68 | 1,2 Hexandiol, Caprylyl Glycol | 0.80 |
| | | Vanillyl Butyl Ether | 0.40 |
| B | Dracorin ® GOC | Glyceryl Oleate Citrate, Caprylic/Capric Triglyceride | 0.30 |
| | Dragoxat ® 89 | Ethylhexyl Isononanoate | 6.00 |
| | Neutral Oil | Caprylic/Capric Triglyceride | 4.00 |
| | SymMollient S | Cetearyl Nonanoate | 2.00 |
| | Ethanol | Alcohol denat. | 20.00 |
| | SymDeo ® B 125 | 2-Methyl-5-Cyclohexylpentanol | 0.50 |
| | Frescolat ® X-cool | Menthyl Ethylamido Oxalate | 0.50 |
| | SymRepair ® 100 | Hexyldecanol, Bisabolol, Cetylhydroxyproline Palmitamide, Stearic Acid, *Brassica Campestris* (Rapeseed) Sterols | 1.00 |
| C | Cosmedia ® SP | Sodium Polyacrylate | 1.20 |
| D | Tapioca Pure | Tapioca Starch | 1.00 |

TABLE 9-continued

Gel cream for feet (Amounts in % b.w.)

| Phase | Ingredients | INCI | Amount |
|---|---|---|---|
| E | Sodium Hydroxide 10% | Sodium Hydroxide | 0.65 |
|   | Fragrance | Parfum | 1.0 |

TABLE 10

Gentle scalp scrub (Amounts in % b.w.)

| Phase | Ingredients | INCI | Amount |
|---|---|---|---|
| A | Lanette ® O | Cetearyl Alcohol | 5.00 |
|   | Emulsiphos ® | Potassium Cetyl Phosphate, Hydrogenated Palm Glycerides | 1.00 |
|   | SymMollient ® S | Cetearyl Nonanoate | 2.00 |
|   | SymSitive ® 1609 | Pentylene Glycol, 4-t-Butylcyclohexanol | 1.00 |
|   | Crinipan ® AD | Climbazole | 0.40 |
| B | Water | Aqua | Ad 100 |
|   | Jaguar ® C-500 | Guar Hydroxypropyltrimonium Chloride | 0.60 |
|   | Symdiol ® 68 | 1,2 Hexandiol, Caprylyl Glycol | 0.80 |
|   |   | Vanillyl Butyl Ether | 0.50 |
| C | Aristoflex ® AVC | Ammonium Acryloyoldimetyhltaurate/VP Copolymer | 0.50 |
| D | SymCalmin ® | Pentylene Glycol, Butylene Glycol, Hydroxyphenylpropamidobenzoic Acid | 0.10 |
| E | Frescolat ® Plus | Methyl, Menthyl Lactate | 0.50 |
| F | Hydroviton ® Plus | Aqua, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium Hyaluronate, Glucose | 1.00 |
| G | Fragrance | Parfum | 1.00 |
| H | Citric Acid 10% Solution | Aqua, Citric Acid | 0.20 |
| I | Gotalene ® 120 Black | Polyethylene | 1.00 |

TABLE 11

Rescue After Shave (Amounts in % b.w.)

| Phase | Ingredients | INCI | Amount |
|---|---|---|---|
| A | Water | Aqua | Ad 100 |
|   | Carbopol ® Ultrez 21 Polymer | Acrylates/C10-30 Alkyl Acrylate Crosspolymer | 0.60 |
| B | Glycerol | Glycerol | 2.00 |
| C | Biotive ® L-Arginine | Arginine | 0.50 |
| D | Ethanol | Alcohol denat. | 10.00 |
| E | Hydrolite ® 5 | Pentylene Glycol | 5.00 |
|   |   | Vanillyl Butyl Ether | 0.60 |
|   | Frescolat ® MGA | Menthone Glycerin Acetal | 0.50 |
|   | Xiameter ® PMX-345 | Cyclopentasiloxane, Cyclohexasiloxane | 4.00 |
|   | SymRelief ® 100 | Zingiber Officinale Root Extract | 0.10 |
| F | Tapioca Pure | Tapioca Starch | 2.00 |
| G | Fragrance | Parfum | 1.00 |

TABLE 12

Rescue After Shave (Amounts in % b.w.)

| Phase | Ingredients | INCI | Amount |
|---|---|---|---|
| A | Water | Aqua | Ad 100 |
|   | Carbopol ® Ultrez 21 Polymer | Acrylates/C10-30 Alkyl Acrylate Crosspolymer | 0.45 |
| B | Sodium Hydroxide 10% Sol. | Sodium Hydroxide | 0.40 |
| C | SymGlucan ® | Aqua, Glycerin, 1,2-Hexandiol, Caprylyl Glycol, Beta-Glucan | 5.00 |
|   |   | Vanillyl Butyl Ether | 0.30 |
|   | Aloe Vera Gel Concentrate | Aloe Barbadensis Leaf Juice | 0.50 |
| D | SymOcide ® PH | Phenoxyethanol, Hydroxyacetophenone, Caprylyl Glycol, Aqua | 1.20 |
|   | SymRelief ® 100 | Zingiber Officinale Root Extract | 0.10 |
|   | Dracorin ® GOC | Glyceryl Oleate Citrate, Caprylic/Capric Triglyceride | 1.00 |

TABLE 12-continued

Rescue After Shave (Amounts in % b.w.)

| Phase | Ingredients | INCI | Amount |
|---|---|---|---|
|  | Frescolat ® ML Cryst. | Menthyl Lactate | 1.00 |
|  | Fragrance | Parfum | 0.30 |
| E | Sodium Hydroxide 30% sol. | Sodium Hydroxide | 0.37 |

TABLE 13

Intimate Silky Veil (Amounts in % b.w.)

| Phase | Ingredients | INCI | Amount |
|---|---|---|---|
| A | Dracorin ® GOC | Glyceryl Oleate Citrate, Caprylic/Capric Triglyceride | 2.20 |
|  | PCL-Liquide ® 100 | Ceterayl Ethylhexanoate | 3.00 |
|  | SymCalmin ® | Pentylene Glycol, Butylene Glycol, Hydroxyphenylpropamidobenzoic Acid | 1.00 |
|  |  | Vanillyl Butyl Ether | 0.30 |
|  | Frescolat ® X-cool | Menthyl Ethylamido Oxalate | 0.50 |
|  | Fragrance | Parfum | 0.20 |
| B | Water | Aqua | Ad 100 |
|  | Pemulen TR-2 Polymeric Emulsifier | Acrylates/C10-30 Alkyl Acrylate Crosspolymer | 0.20 |
|  | SymOcide ® PH | Phenoxyethanol, Hydroxyacetophenone, Caprylyl Glycol, Aqua | 1.30 |
|  | Potassium Sorbate | Potassium Sorvate | 0.10 |
|  | Extrapone ® Camomille GW | Glycerin, Aqua, *Chamomilla Recutita* Flower Extract | 0.50 |
| C | Sodium Hydroxide 10% Sol. | Sodium Hydroxide | 0.45 |

TABLE 14

Deodorant Roll On (Amounts in % b.w.)

| Phase | Ingredients | INCI | Amount |
|---|---|---|---|
| A | SymSitive ® 1609 | Pentylene Glycol, 4-tButylcyclohexanol | 1.20 |
|  | SymWhite ® 377 | Phenylethyl Resorcinol | 0.30 |
|  | Arlacel 165 | Glyceryl Stearate, PEG-100 Stearate | 3.00 |
|  | Brij ® 72 | Steareth-2 | 0.30 |
|  | Brij ® 721 P | Steareth-21 | 2.50 |
|  | Arlamol PS15 | PPG15 Stearyl Ether | 2.00 |
|  | Lanette ® O OR | Cetearyl Alcohol | 1.00 |
|  | Copherol ® 1250 | Tocopheryl Acetate | 0.50 |
| B | Water | Aqua | Ad 100 |
|  | Glycerin | Glycerin | 2.0 |
|  | EDTA NA 2 | Disodium EDTA | 0.10 |
|  | SymTriol ® | Caprylyl Glycol, 1,2-Hexandiol, Methylbenzyl Alcohol | 0.60 |
|  |  | Vanillyl Butyl Ether | 0.30 |
|  | Veegum HV | Magnesium Aluminium Silicate | 1.00 CC |
| C | Water | Aqua | 3.00 |
|  | Covastyle MBS | Sodium Metabisulfite | 0.15 |
| D | Oxynex ST liquid | Diethylhexyl Syringylidemalonate, Caprylic Capric Triglycerides | 0.10 |
|  | SymDeo ® B125 | 2-Methyl-5-cyclohexylpentanol | 0.50 |
| E | Extrapone ® Aquamarine GW | Aqua, Glycerin, Xanthan Gum, Aquamarine Powder | 0.50 |
| G | Fragrance | Parfum | 1.00 |

TABLE 15

Body Wash Scrub (Amounts in % b.w.)

| Phase | Ingredients | INCI | Amount |
|---|---|---|---|
| A | Sweet Almond Oil | *Prunus Amygdalus Dulcis* Oil | 20.00 |
|   | Tocopheryl Acetate | Tocopheryl Acetate | 0.50 |
|   | Neutral Oil | Carylic Capric Triglyceride | 8.00 |
|   | Fragrance | Parfum | 1.50 |
|   | Caropol ® ETD 2020 | Acrylates/C10-30 Alkyl Acrylate Crosspolymer | 1.10 |
| B | Crodasinic ® LS-30 | Sodium Lauroyl Sarcosinate | 35.00 |
|   | Protelan ® AGL | Sodium Lauroyl Glutamate | 8.00 |
|   | Proteol ® APL | Sodium Cocoyl Apple Amino Acids | 2.00 |
|   | SymOcide ® PL | Phenoxyethanol, Decylene Glycol, 1,2-Hexandiol | 1.00 |
|   |   | Vanillyl Butyl Ether | 0.25 |
| C | Aqua | Water | Ad 100 |
| D | Sodium Hydroxide 30% Sol. | Sodium Hydroxide | 0.70 |
| E | Hydroviton ® Plus | Aqua, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium Hyaluronate, Glucose | 4.00 |
|   | Extrapone ® Lotus Flower | Aqua, Butylene Glycol, *Nelumbo Nucifera* Flower Extract | 1.00 |
| F | Lipo Luffa 30/100 | *Luffa Cylindrica* Fruit | 1.00 |

TABLE 16

Calming Scalp Shampoo (Amounts in % b.w.)

| Phase | Ingredients | INCI | Amount |
|---|---|---|---|
| A | Water | Aqua | Ad 100 |
|   | SymSaye ® H | Hydroxyacetophenone | 0.50 |
|   | Hydrolite ® CG | Caprylyl Glycol | 0.50 |
|   |   | Vanillyl Butyl Ether | 0.30 |
|   | Carbopol ® Aqua SF-2 Polymer | Acrylates Crosspolymer-4 | 7.00 |
|   | Texapon ® NSO IS | Sodium Laureth Sulfate Aqua | 40.00 |
|   | Sodium Hydroxide 10% Sol. | Sodium Hydroxide | 0.50 |
| B | Tego ® Betain CK KB5 | Cocamidopropyl Betaine, Aqua, Sodium Chloride | 7.00 |
|   | Ucare ® Polymer JR 400 | Polyquaternium-10 | 0.20 |
| C | Euperlan ® PK 4000 | Glycol Distearate, Laureth-4, Cocamidopropyl Betaine | 3.00 |
| D | Fragrance | Parfum | 1.00 |
| E | Hydroviton ® Plus | Aqua, Pentylene Glycol, Glycerin, Fructose, Urea, Citric Acid, Sodium Hydroxide, Maltose, Sodium PCA, Sodium Chloride, Sodium Lactate, Trehalose, Allantoin, Sodium Hyaluronate, Glucose | 2.00 |
|   | Sweet Almond Oil | *Prunus Amygdalus Dulcis* Oil | 0.20 |
|   | Extrapone ® Acacia Honey | Propylene Glycol, Miel | 0.20 |
|   | SymCalmin ® | Pentylene Glycol, Butylene Glycol, Hydroxyphenylpropamidobenzoic Acid | 0.10 |
| F | Citric Acid 10% Sol. | Aqua, Citric Acid | 1.00 |
| G | Sodium Chloride | Sodium Chloride | 0.20 |

TABLE 17

After Shave Gel (Amounts in % b.w.)

| Phase | Ingredients | INCI | Amount |
|---|---|---|---|
| A | SymSol ® PF-3 | Aqua, Pentylene Glycol, Sodium Lauryl Sulfoacetate, Sodium Oleyl Sarcosinate, Sodium Chloride, Disodium Sulfoacetate, Sodium Oleate, Sodium Sulfate | 3.00 |
|   | SymSitive ® 1609 | Pentylene Glycol, 4-tButylcyclohexanol | 1.00 |
|   | Frescolat ® ML | Menthyl Lactate | 0.30 |
| B | Fragrance | Parfum | 0.15 |
|   | Glycerin | Glycerin | 5.00 |
|   | Water | Aqua | Ad 100 |
|   | Pemulen ® TR-2 Polymeric Emulsifier | Acrylates/C10-30 Alkyl Acrylate Crosspolymer | 1.00 |
|   | Extrapone ® Glacier Water GW | Glycerin, Aqua | 1.00 |
|   | SymCalmin ® | Pentylene Glycol, Butylene Glycol, | 0.50 |

TABLE 17-continued

After Shave Gel (Amounts in % b.w.)

| Phase | Ingredients | INCI | Amount |
|---|---|---|---|
| | | Hydroxyphenylpropamidobenzoic Acid | |
| | Dragosine ® | Carnosin | 0.10 |
| | Hydrolite ® 5 | Pentylene Glycol | 5.00 |
| | | Vanillyl Butyl Ether | 0.60 |
| | Sodium Hydroxide 10% Sol. | Sodium Hydroxide | 3.15 |
| C | Ethanol | Alcohol denat. | 10.00 |
| | Colour | Colour | 0.50 |

TABLE 18

Deo Stick (Amounts in % b.w.)

| Phase | Ingredients | INCI | Amount |
|---|---|---|---|
| A | Dragoxat ® 89 | Ethylhexyl Isononanoate | 1.00 |
| | 1,2 Propylene Glycol | Propylene Glycol | 54.50 |
| | Sodium Stearate | Sodium Stearate | 8.00 |
| | Hydrolite ® 5 | Pentylene Glycol | 0.50 |
| | | Vanillyl Butyl Ether | 0.40 |
| | Glycerin | Glycerine | 20.00 |
| | Water | Aqua | Ad 100 |
| B | SymDeo ® B 125 | 2-Methyl 5-Cyclohexylpentanol | 0.50 |
| | Fragrance | Parfüm | 1.50 |

TABLE 19

Hand and body cream (Amounts in % b.w.)

| Ingredients | INCI | Amount |
|---|---|---|
| Dracorin ® GOC | Glyceryl Oleate Citrate. Caprylic/Capric Triglyceride | 2.00 |
| PCL-Solid | Stearyl Heptanoate. Stearyl Caprylate | 2.50 |
| Lanette ® O | Cetearyl Alcohol | 1.50 |
| Cutina ® GMS-V | Glyceryl Stearate | 1.00 |
| Dragoxat ® 89 | Ethylhexyl Isononanoate | 3.00 |
| PCL-Liquid 100 | Cetearyl Ethylhexanoate | 7.00 |
| Isodragol® | Triisononanoin | 4.00 |
| Xiameter ® PMX-0345 Cyclosiloxane | Cyclopentasiloxane (and) Cyclohexasiloxane | 0.50 |
| Water | Water (Aqua) | Ad 100 |
| Carbopol ® Ultrez 21 | Acrylates/C10-30 Alkyl Acrylate Crosspolymer | 0.20 |
| Keltrol ® CG-RD | Xanthan Gum | 0.10 |
| Glycerol 85 P. | Glycerol | 3.00 |
| DragoBetaGlucan | Water (Aqua). Butylene Glycol. Glycerol. Avena Sativa (Oat) Kernel Extract | 1.50 |
| Potassium Sorbat | Potassium Sorbate | 0.10 |
| Sodium Hydroxide 10% solution | Sodium Hydroxide | 0.50 |
| Perfume oil | Parfum | 0.20 |
| Euxyl ® K300 | Methyl-. Butyl-. Ethyl-. Propyl. Isobutylparaben. Phenoxyethanol. | 0.30 |
| | Vanillyl butyl ether | 0.20 |
| SymDiol ® 68 | 1,2-hexandiol and 1,2-octandiol | 0.10 |

TABLE 20

Face cream (Amounts in % b.w.)

| Ingredients | INCI | Amount |
|---|---|---|
| Emulsiphos® | Potassium Cetyl Phosphate. Hydrogenated Palm Glycerides | 1.50 |

TABLE 20-continued

Face cream (Amounts in % b.w.)

| Ingredients | INCI | Amount |
|---|---|---|
| Cutina ® GMS-V | Glyceryl Stearate | 1.70 |
| Lanette ® O | Cetearyl Alcohol | 3.00 |
| Tegosoft ® MM | Myristyl Myristate | 1.00 |
| PCL-Liquid 100 | Cetearyl Ethylhexanoate | 1.00 |
| Isodragol® | Triisononanoin | 3.00 |
| Dragoxat ® 89 | Ethylhexyl Isononanoate | 4.00 |
| Avocado Oil | Persea Gratissima (Avocado) Oil | 3.00 |
| Abil ® 350 | Dimethicone | 0.50 |
| Covi-ox ® T-70 | Tocopherol | 0.10 |
| Edeta ® BD | Disodium EDTA | 0.10 |
| Carbopol ® Ultrez 21 | Acrylates/C10-30 Alkyl Acrylate Crosspolymer | 0.30 |
| Keltrol ® CG-RD | Xanthan Gum | 0.150 |
| Water | Water (Aqua) | Ad 100 |
| Glycerol 99.5 P. | Glycerol | 4.00 |
| Propylene Glycol-1.2 99 P GC | Propylene Glycol | 3.00 |
| Sym Matrix® | Maltodextrin. Rubus Fruticosus (Blackberry) Leaf Extract | 0.50 |
| Sodium Hydroxide 10% solution | Sodium Hydroxide | 0.50 |
| Perfume oil | Parfum | 0.30 |
| Euxyl ® K712 | Sodium Benzoate. Potassium Sorbate | 0.20 |
| | Vanillyl butyl ether | 0.25 |
| SymDiol ® 68 | 1,2-hexandiol and 1,2-octandiol | 0.35 |

TABLE 21

Moisturizing body care cream (Amounts in % b.w.)

| Ingredient | Amount |
|---|---|
| PEG-7 hydrogenated castor oil | 6.00 |
| Cetearyl ethyl hexanoate | 10.00 |
| Isopropyl myristate | 5.00 |
| Mineral oil | 7.00 |
| Shea Butter (Butyrospermum parkii) | 0.50 |
| Aluminum stearate | 0.50 |
| Magnesium stearate | 0.50 |
| Bisabolol | 0.20 |
| Quaternium-18-Hectorit | 0.70 |
| Dipropylene glycol | 5.0 |
| Magnesium sulfate | 0.70 |
| Pentylene glycol | 4.00 |
| Perfume oil | 0.30 |
| Preservative (Phenoxyethanol) | 0.20 |
| Capsaicin | 0.20 |
| 1,2-heptandiol | 0,20 |
| Aqua dem. | Ad 100 |

TABLE 22

Anti-wrinkle cream (Amounts in % b.w.)

| Ingredients | Amount |
|---|---|
| Glyceryl Stearate Citrate | 1.00 |
| Glyceryl Laurate | 1.00 |
| Cetearyl Alcohol (and) Myristyl Myristate | 3.00 |
| Cetearyl Ethylhexanoate | 4.00 |
| Mineral oil | 4.00 |
| Cyclopentasiloxane, Cyclohexasiloxane | 0.50 |
| Acrylates/C10-30 Alkyl Acrylate Crosspolymer | 0.20 |
| Water | Ad 100 |
| 1.2-Hexanediol | 2.00 |
| Sodium Hydroxide 10% solution | 0.10 |
| Narcissus Tazetta Bulb Extract | 1.00 |
| Perfume oil | 0.30 |
| Preservative (Phenoxyethanol) | 0.50 |
| Vanillyl butyl ether | 0.25 |
| 1,2-heptandiol | 0.25 |

TABLE 23

Functional skin oil for disinfection (Amounts in % b.w.)

| Ingredients | INCI | Amount |
|---|---|---|
| Neutral Oil | Caprylic/Capric Triglyceride | Ad 100 |
| Sweet Almond Oil | *Prunus Dulcis* | 20.00 |
| Dragoxat ® 89 | Ethylhexyl Isononanoate | 4.00 |
| Isopropyl Palmitate | Isopropyl Palmitate | 6.00 |
| PCL-Liquid 100 | Cetearyl Ethylhexanoate | 15.00 |
| Dragosantol ® 100 | Bisabolol | 0.20 |
| Retinyl Acetate In Oil (1 Mio. Ie/G) | Retinyl Acetate | 0.50 |
| Vitamin E Acetate | Tocopheryl Acetate | 0.50 |
| Covi-ox ® T-70 | Tocopherol | 0.10 |
| Perfume oil | Parfum | 0.30 |
| Preservative | Methyl-. Butyl-. Ethyl-. Propylparaben | 0.30 |
|  | Capsaicin | 0.20 |
| SymDiol ® 68 | 1,2-hexandiol and 1,2-octandiol | 0.20 |

TABLE 24

Septic wound cream (Amounts in % b.w.)

| Ingredients (INCI) | Amount |
|---|---|
| Sorbitan Isostearate. Hydrogenated Castor Oil. Ceresin. Beeswax (*Cera Alba*) | 6.00 |
| Petrolatum | 21.00 |
| *Cera Alba* | 5.00 |
| Cetearyl Alcohol | 7.00 |
| *Prunus Dulcis* | 7.00 |
| Lanolin | 5.00 |
| Paraffinum Liquidum | 12.00 |
| Perfume oil P1. P2. P3 or P4 | 0.30 |
| Water (Aqua) | Ad 100 |
| Panthenol | 7.00 |
| Magnesium Sulfate | 0.70 |
| Pentylene Glycol | 1.00 |
| Tocopheryl Acetate | 1.00 |
| Octenidine dihydrochloride | 0.10 |
| Phenoxyethanol | 0.50 |
| Vanillyl butyl ether | 0.25 |
| 1,2-octandiol | 0.25 |

TABLE 25

Moisturizing and disinfecting face mask (Amounts in % b.w.)

| Ingredients | INCI | Amount |
|---|---|---|
| Water | Water (Aqua) | Ad 100 |
| Stabileze QM | PVM/Ma Decadiene Crosspolymer | 0.50 |
| Biotive ® L-Arginine | Arginine | 0.75 |
| Actipone ® *Laminaria Saccharina* GW | Glycerol. Water (Aqua). *Laminaria Saccharina* Extract | 1.00 |
| Extrapone ® Cucumber | Water (Aqua). Propylene Glycol. *Cucumis Sativus* (Cucumber) Juice | 1.00 |
| Glycerol 99.5 P. | Glycerol | 7.00 |
| Neo Actipone ® Soap Nutshell | *Sapindus Mukurossi* Peel Extract | 0.50 |
| Colour I | Colour | 0.01 |
| Hydrolite ® 5 | Pentylene Glycol | 5.00 |
| Solubilizer | PEG-40 Hydrogenated Castor Oil. Trideceth-9. Water (Aqua) | 0.60 |
| Perfume oil | Parfum | 0.08 |
| Preservative | Phenoxyethanol | 0.40 |
|  | Vanillyl butyl ether | 0.20 |
| SymDiol ® 68 | 1,2-hexandiol and 1,2-octandiol | 0.20 |

TABLE 26

Sprayable disinfecting gel (Amounts in % b.w.)

| Ingredients | INCI | Amount |
|---|---|---|
| Water | Water (Aqua) | Ad 100 |
| Stabileze QM | PVM/Ma Decadiene Crosspolymer | 0.25 |
| Sodium Hydroxide 10% solution | Sodium Hydroxide | 0.40 |
| Coffein pure | Caffeine | 0.50 |
| Extrapone ® Horse Chestnut | Propylene Glycol. Water (Aqua). Glucose. *Aesculus Hippocastanum* (Horse Chestnut) Seed Extract. Lactic Acid | 1.00 |
| Hydrolite ® 5 | Pentylene Glycol | 3.00 |
| 1.3 Butylene Glycol | Butylene Glycol | 5.00 |
| Biotive ® Esculin Sesquihydrate | Esculin | 0.30 |
| Ethanol 96% | Alcohol Denat. | 10.00 |
| Solubilizer | PEG-40 Hydrogenated Castor Oil. Trideceth-9. Water (Aqua) | 0.50 |
| Perfume oil | Parfum | 0.20 |
| Octenidine dihydrochloride |  | 0.10 |
| Preservative | Phenoxyethanol | 0.70 |
|  | Vanillyl butyl ether | 0.20 |
| SymDiol ® 68 | 1,2-hexandiol and 1,2-octandiol | 0.10 |

TABLE 27

Mineral wash and cleaning gel (Amounts in % b.w.)

| Ingredients | INCI | Amount |
|---|---|---|
| Water | Water (Aqua) | Ad 100 |
| Pionier ® NP 37 G | Sodium Carbomer | 1.50 |
| SymSol ® PF-3 | Water (Aqua). Pentylene Glycol. Sodium Lauryl Sulfoacetate. SodiumOleoyl Sarcosinate. Sodium Chloride. Disodium Sulfoacetate. SodiumOleate. Sodium Sulfate | 5.00 |
| Hydroyiton ® 24 | Water (Aqua). Pentylene Glycol. Glycerol. Sodium Lactate. Lactic Acid. Serine. Urea. Sorbitol. Sodium Chloride. Allantoin | 1.00 |
| Extrapone ® Silk GW | Water (Aqua). Glycerol. Hydrolyzed Silk | 1.00 |
| Hydrolite ® 5 | 1,2-heptandiol | 4.00 |
| Actipearls Red Star # DH10402/6 | Water (Aqua). Propylene Glycol. Algin. Gellan Gum. Xanthan Gum. CalciumChloride. CI 12490 (Pigment Red 5). Mica (CI 77019). Titanium Dioxide (CI 77891) | 1.00 |
| Perfume oil | Parfum | 0.50 |
| 3-Phenylpropanol |  | 0.70 |
|  | Vanillyl hexyl ether | 0.30 |

TABLE 17

Anti-acne wash (Amounts in % b.w.)

| Ingredients (IN Cl) | Amount |
|---|---|
| Water (Aqua) | 45.70 |
| Polyquaternium-7 | 0.50 |
| Cocamidopropyl Betaine 9.000 | 9.00 |
| Coco Glucoside 2.000 | 2.00 |
| Polysorbate 80. Glycerol. *Gossypium Herbaceum*. (Cotton) Seed Oil. Water (Aqua) | 1.00 |
| Trideceth-9. PEG-5 Ethylhexanoate. Water (Aqua) | 1.00 |
| Glycereth-90 Isostearate. Laureth-2 | 0.50 |
| Sodium Laureth Sulfate 37.000 | 37.00 |
| Glycerol. *Triticum Vulgare* (Wheat) Gluten. Water (Aqua) | 1.00 |
| Sodium Chloride | 0.30 |
| Perfume oil | 1.00 |
| Phenoxyethanol. Methylparaben. Ethylparaben. Butylparaben. Propylparaben. Isobutylparaben | 0.30 |

TABLE 17-continued

Anti-acne wash (Amounts in % b.w.)

| Ingredients (IN Cl) | Amount |
|---|---|
| Vanillyl butyl ether | 0.25 |
| 1,2-octandiol | 0.25 |

TABLE 28

Cosmetic sun protection composition (Amounts in % b.w.)

| Ingredient | Amount |
|---|---|
| Ethylhexyl cinnamic acid | 7.50 |
| Benzophenon-3 | 2.00 |
| Polyglyceryl dimer soyate | 0.80 |
| Sorbitane stea rate | 1.00 |
| Tocopheryl acetate | 0.50 |
| Glyceryl stearate. PEG-100 Stearate | 3.00 |
| PEG-40. hydrogenated castor oil | 1.00 |
| Titanium dioxide. aluminum oxide hydrate. Dimethicon/Methicon Copolymer | 3.00 |
| *Butyrospermum parkii* (Shea Butter) | 1.00 |
| $C_{12-15}$ alkyl benzoate | 6.50 |
| Butylene glycol | 5.00 |
| Xanthan gum | 0.30 |
| Disodium EDTA | 0.10 |
| Allantoin | 0.10 |
| Polyacryl amide. $C_{13-14}$ isoparaffin. Lau reth-7 | 1.00 |
| Pentylene glycol | 5.00 |
| 4-t Butylcyclohexanol | 1.00 |
| Perfume oil | 0.30 |
| Preservatives (Methyl-. Butyl-. Ethyl-. Propylparaben. Phenoxyethanol) | 0.30 |
| Vanillyl butyl ether | 0.35 |
| 1,2-heptandiol | 0.25 |
| Aqua dem. | Ad 100 |

TABLE 29

Sun protection spray (Amounts in % b.w.)

| Ingredients | INCI | Amount |
|---|---|---|
| Water. demineralized | Water (aqua) | 69.50 |
| Glycerol | Glycerol | 4.00 |
| 1.3 butylene glycol | Butylene glycol | 5.00 |
| D-Panthenol | Panthenol | 0.50 |
| Lara Care A-200 | Galactoarabinan | 0.25 |
| Baysilone oil M 10 | Dimethicone | 1.00 |
| Edeta BD | Disodium EDTA | 0.10 |
| Copherol 1250 | Tocopheryl acetate | 0.50 |
| Cetiol OE | Dicaprylyl ether | 3.00 |
| Neo Heliopan ® HMS | Homosalate | 5.00 |
| Neo Heliopan ® AV | Ethylhexyl methoxycinnamate | 6.00 |
| Neo Heliopan ® 357 | Butyl methoxydibenzoylmethane | 1.00 |
| Corapan TQ | Diethylhexylnaphthalate | 2.00 |
| Alpha Bisabolol | Bisabolol | 0.10 |
| Pemulen TR-2 | Acrylates/C10-30 alkyl acrylate crosspolymer | 0.25 |
| NaOH. 10% | Sodium hydroxide | 0.60 |
| Perfume oil Pl. P2. P3 or P4 | Fragrance | 0.20 |
| Phenoxyethanol | Phenoxyethanol | 0.40 |
| Solbrol M | Methylparaben | 0.10 |
| Solbrol P | Propylparaben | 0.10 |
|  | Vanillyl butyl ether | 0.50 |
| Hydrolite 5 | 1,2-heptandiol | 0.25 |

TABLE 30

Sunscreen spray O/W. SPE 15-20 (Amounts in % b.w.)

| Ingredients | INCI | Amount |
|---|---|---|
| Dracorin ® GOC | Glyceryl Oleate Citrate. Caprylic/Capric Triglyceride | 2.00 |
| Corapan ® TQ | Diethylhexyl 2.6-Naphthalate | 3.00 |
| Neo Heliopan ® HMS | Homosalate | 7.00 |
| Neo Heliopan ® OS | Ethylhexyl Salicylate | 5.00 |
| Neo Heliopan ® 357 | Butyl Methoxydibenzoylmethane | 3.00 |
| Isoadipate | Diisopropyl Adipate | 6.00 |
| Baysilone ® Oil M10 | Dimethicone | 1.00 |
| Edeta ® BD | Disodium EDTA | 0.10 |
| Vitamin E Acetate | Tocopheryl Acetate | 0.50 |
| Dragosantol ® 100 | Bisabolol | 0.10 |
| Pemulen ® TR-2 | Acrylates/C10-30 Alkyl Acrylate Crosspolymer | 0.25 |
| Water | Water (Aqua) | Ad 100 |
| Glycerol 99.5 P. | Glycerol | 4.00 |
| Butylene Glycol | Butylene Glycol | 5.00 |
| Neo Heliopan ® Hydro (103089). used as 25% aq. solution neutralized with Biotiye ® L-Arginine | Phenylbenzimidazole Sulfonic Acid | 8.00 |
| Biotiye ® L-Arginine | Arginine | 0.55 |
| Perfume oil | Fragrance | 0.40 |
| Sobrol M | Methylparaben | 0.30 |
|  | Vanillyl butyl ether | 0.60 |
| SymDiol ® 68 | 1,2-hexanediol and 1,2-octandiol |  |

TABLE 31

Sun protection soft cream (W/O). SPF 40 (Amounts in % b.w.)

| Ingredients | INCI | Amount |
|---|---|---|
| Dehymuls PGPH | Polyglyceryl-2 dipolyhydroxystearate | 5.00 |
| Copherol 1250 | Tocopheryl acetate | 0.50 |
| Permulgin 3220 | Ozocerite | 0.50 |
| Zinc stearate | Zinc stearate | 0.50 |
| Tegosoft TN | C12-15 Alkyl benzoate | 10.00 |
| Neo Heliopan ® E1000 | Isoamyl-p-methoxycinnamate | 2.00 |
| Neo Heliopan ® 303 | Octocrylene | 5.00 |
| Neo Heliopan ® MBC | 4-Methylbenzylidene camphor | 3.00 |
| Zinc oxide. neutral | Zinc oxide | 5.00 |
| Water. distilled | Water (aqua) | Add 100 |
| EDETA BD | Disodium EDTA | 0.10 |
| Glycerol | Glycerol | 4.00 |
| Magnesium sulfate | Magnesium sulfate | 0.50 |
| Perfume oil | Parfum | 0.30 |
| SymDiol ® 68 | 1,2 hexanediol (and) 1,2 octandiol | 0.30 |
|  | Vanillyl butyl ether | 0.30 |

TABLE 32

Sun protection milk (W/O) (Amounts in % b.w.)

| Ingredients | INCI | Amount |
|---|---|---|
| Dehymuls PGPH | Polyglyceryl-2 dipolyhydroxystearate | 3.00 |
| Beeswax 8100 | Beeswax | 1.00 |
| Monomuls 90-0-18 | Glyceryl oleate | 1.00 |
| Zinc stearate | Zinc stearate | 1.00 |
| Cetiol SN | Cetearyl isononanoate | 5.00 |
| Cetiol OE | Dicaprylyl ether | 5.00 |
| Tegosoft TN | C12-15 alkyl benzoate | 4.00 |
| Vitamin E | Tocopherol | 0.50 |
| Neo Heliopan ® OS | Ethylhexyl salicylate | 5.00 |
| Neo Heliopan ® AV | Ethylhexyl methoxycinnamate | 7.50 |
| Uvinul ® T150 | Ethylhexyl triazone | 1.50 |
| Water. distilled | Water (Aqua) | To 100 |
| Trilon BD | Disodium EDTA | 0.10 |
| Glycerol | Glycerol | 5.00 |

TABLE 32-continued

Sun protection milk (W/O) (Amounts in % b.w.)

| Ingredients | INCI | Amount |
|---|---|---|
| Neo Heliopan ® AP 10% solution. neutralized with NaOH | Disodium phenyl dibenzimidazole tetrasulfonate | 15.00 |
| Perfume oil | Parfum | 0.25 |
| Alpha bisabolol | Bisabolol | 0.10 |
| SymOcide ® PT | Phenoxyethanol. Tropolone | 0.25 |
| SymDiol ® 68 | 1,2 hexandiol (and) 1,2 octandiol | 0.10 |
|  | Vanillyl butyl ether | 0.15 |

TABLE 33

After sun gel (Amounts in % b.w.)

| Ingredients | INCI | Amount |
|---|---|---|
| SymSol ® PF-3 | Water (Aqua). Pentylene Glycol. Sodium Lauryl Sulfoacetate. SodiumOleoyl Sarcosinate. Sodium Chloride. Disodium Sulfoacetate. SodiumOleate. Sodium Sulfate | 3.000 |
| Glycerol 99.5 P. | Glycerol | 5.000 |
| SymHelios ® 1031 | Benzylidene Dimethoxydimethylin danone | 0.100 |
| Water | Water (Aqua) | Ad 100 |
| Pemulen ® TR-2 | Acrylates/C10-30 Alkyl Acrylate Crosspolymer | 1.000 |
| D-Panthenol 75 W | Panthenol | 0.500 |
| SymFinity ® 1298 | *Echinacea Purpurea* Extract | 0.100 |
| Extrapone ® Pearl GW | Water (Aqua). Glycerol. Hydrolyzed Pearl. Xanthan Gum | 1.000 |
| Sodium Hydroxide 10% solution | Sodium Hydroxide | 2.500 |
| Ethanol 96 % | Alcohol Denat. | 15.000 |
| Perfume oil | Parfum | 0.20 |
| SymOcide ® PS | Phenoxyethanol. 1.2-Hexanediol. Decyleneglycol | 0.50 |
| SymDiol ® 68 | 1,2 hexandiol (and) 1,2 octandiol | 0.25 |
|  | Vanillyl butyl ether | 0.25 |

TABLE 34

After sun lotion (Amounts in % b.w.)

| Ingredients | Amount |
|---|---|
| Acrylate/C10-30 alkylacrylate crosspolymer | 0.4 |
| Cetearylethyl hexanoate | 15.0 |
| Bisabolol | 0.2 |
| Tocopheryl acetate | 1.0 |
| Panthenol | 1.0 |
| Alcohol | 15.0 |
| Glycerol | 3.0 |
| Perfume oil | 0.30 |
| 1.2-Hexanediol | 0.20 |
| Vanillyl butyl ether | 0.10 |
| Pentylene glycol | 4.0 |
| Aqua dem. | Ad 100 |
| Triethanolamine | 0.2 |

TABLE 35

Silicone emulsion (Amounts in % b.w.)

| Ingredients | Amount |
|---|---|
| Potassium Cetyl Phosphate. Hydrogenated Palm Glycerides | 1.00 |
| Cyclohexasiloxane | 4.00 |
| Cetearyl Alcohol | 1.50 |
| Phenyl Trimethicone | 3.00 |
| Stearyl Heptanoate. Stearyl Caprylate | 3.00 |
| Dimethicone | 1.00 |
| Xanthan Gum | 0.20 |
| Isoamyl p-Methoxycinnamate | 5.00 |
| Water | Ad 100 |
| Methylpropanediol | 3.00 |
| Perfume oil | 0.30 |
| 1.2-Hexanediol | 0.25 |
| Vanillyl butyl ether | 0.25 |

TABLE 36

Microemulsion gel (Amounts in % b.w.)

| Ingredient | Amount |
|---|---|
| Glycerol isostearate | 1.80 |
| Octoxyglycerol | 1.00 |
| Ceteareth-15 | 5.20 |
| PEG-150 Distearate | 1.00 |
| Aluminium chlorohydrate | 5.00 |
| Isotridecylisononanoate | 3.30 |
| Cyclomethicone | 6.60 |
| Perfume oil | 0.70 |
| 1.2-Hexanediol | 0.20 |
| Vanillyl butyl ether | 0.20 |
| Water | Ad 100 |

TABLE 37

Toothpaste (Amounts in % b.w.)

| Ingredients | Amount |
|---|---|
| Water (deionized) | Ad 100 |
| Sorbitol 70% | 45.00 |
| Trisodiumphosphate | 0.10 |
| Saccharin | 0.20 |
| Sodiummonofluorophosphate | 1.14 |
| PEG 1500 | 5.00 |
| Sident 9 (abrasive silica) | 10.00 |
| Sident 22 S (Thickening silica) | 8.00 |
| Sod iumca rboxymethylcel lulose | 1.10 |
| Titanium (IV) oxide | 0.50 |

TABLE 37-continued

Toothpaste (Amounts in % b.w.)

| Ingredients | Amount |
| --- | --- |
| Water (deionized) | 4.50 |
| Sodiumlaurylsulfate (SLS) | 1.50 |
| Flavour | 1.00 |
| Solbrol M (Sodium salt) (Methylparaben) | 0.15 |
| 1.2-Octandiol | 0.20 |
| Capsaicin | 0.20 |

TABLE 38

Toothpaste with zinc citrate (Amounts in % b.w.)

| Ingredients | Amount |
| --- | --- |
| Water (deionized) | Ad 100 |
| Sorbitol 70% | 45.00 |
| Trisodiumphosphate | 0.10 |
| Saccharin | 0.20 |
| Sodiummonofluorophosphate | 1.14 |
| PEG 1500 | 5.00 |
| Sident 9 (abrasive silica) | 10.00 |
| Sident 22 S (Thickening silica) | 8.00 |
| Sodiumcarboxymethylcellulose | 1.10 |
| Zinc citrate | 1.00 |
| Titanium (IV) oxide | 0.50 |
| Water (deionized) | 4.50 |
| Sodiumlaurylsulfate (SLS) | 1.50 |
| Flavour | 1.00 |
| SymDiol ® 68 | 0.25 |
| Sanshool I + II | 0.10 |

TABLE 39

Mouth rinse (Amounts in % b.w.)

| Ingredients | Amount |
| --- | --- |
| Ethylalcohol | 10.00 |
| Cremophor CO 40 (PEG 40 hydrogenated castor oil) | 1.00 |
| Flavour | 0.25 |
| Water (deionized) | To 100.00 |
| Sorbitol 70% | 5.00 |
| Sodiumsaccharin 450 | 0.07 |
| Sodiumfluoride | 0.18 |
| Benzoic acid | 0.12 |
| SymDiol ® 68 | 0.20 |
| Nonylic acid vanillyl amide | 0.10 |

TABLE 40

Gel dental cream (Amounts in % b.w.)

| Ingredients | Amount |
| --- | --- |
| Na carboxymethylcellulose | 0.40 |
| Sorbitol 70 %. in water | 72.00 |
| Polyethylene glycol (PEG) 1500 | 3.00 |
| Na saccarinate | 0.07 |
| Na fluoride | 0.24 |
| Flavor | 1.00 |
| Abrasive silica | 11.00 |
| Thickening silica | 6.00 |
| Sodium dodecyl sulfate (SDS) | 1.40 |
| Dist. water | Ad 100 |
| p-Hydroxybenzoic acid (PHB) ethyl ester | 0.15 |
| SymDiol ® 68 | 0.15 |
| Spilanthol | 0.05 |

TABLE 41

Dental cream against plaque (Amounts in % b.w.)

| Ingredients | Amount |
| --- | --- |
| Carrageenan | 0.90 |
| Glycerol | 15.00 |
| Sorbitol 70 %. in water | 25.00 |
| PEG 1000 | 3.00 |
| Na fluoride | 0.24 |
| Tetrapotassium diphosphate | 4.50 |
| Tetrasodium diphosphate | 1.50 |
| Na saccarinate | 0.40 |
| Precipitated silica | 20.00 |
| Titanium dioxide | 1.00 |
| Triclosan | 0.30 |
| Spearmint flavor (comprising 60 wt.% I-carvone and 25 wt.% I-menthol) | 1.00 |
| Sodium dodecyl sulfate | 1.30 |
| Dist. water | Ad 100 |
| Benzylalcohol | 0.50 |
| SymDiol ® 68 | 0.15 |
| Vanillyl butyl ether | 0.10 |

TABLE 32

Dental cream for sensitive teeth (Amounts in % b.w.)

| Ingredients | Amount |
| --- | --- |
| Na carboxymethylcellulose | 0.70 |
| Xanthan gum | 0.50 |
| Glycerol | 15.00 |
| Sorbitol 70 %. in water | 12.00 |
| Potassium nitrate | 5.00 |
| Sodium monofluorophosphate | 0.80 |
| Na saccarinate | 0.20 |
| Flavor | 1.00 |
| Ca-carbonate | 35.00 |
| Silicon dioxide | 1.00 |
| Sodium dodecyl sulfate (SDS) | 1.50 |
| PHB methyl ester and PHB propyl ester | 0.20 |
| SymDiol ® 68 | 0.25 |
| Vanillyl butyl ether | 0.25 |
| Dist. water | Ad 100 |

TABLE 33

Tooth cream and mouthwash 2-in-1 product (Amounts in % b.w.)

| Ingredients | Amount |
| --- | --- |
| Sorbitol | 40.00 |
| Glycerol | 20.00 |
| Ethanol | 5.00 |
| Water | Ad 100 |
| Na monofluorophosphate | 0.75 |
| Saccharin | 0.20 |
| Sident 9 (abrasive silicon dioxide) | 20.00 |
| Sident 22S (thickening silicon dioxide) | 2.00 |
| Sodium carboxymethylcellulose | 0.30 |
| Sodium lauryl sulfate (SDS) | 1.20 |
| Color (Suspension. 1% in water) C.I. Pigment Blue 15 | 0.50 |
| Flavor | 0.90 |
| Solbrol M. sodium salt (methylparaben. Sodium salt) | 0.20 |
| Hydrolite ® 5 | 0.15 |
| Vanillyl butyl ether | 0.15 |

TABLE 34

Ready-to-use mouthwash with fluoride (Amounts in % b.w.)

| Ingredients | Amount |
|---|---|
| Ethanol | 7.00 |
| Glycerol | 12.00 |
| Na fluoride | 0.05 |
| Pluronic F-127 ® (BASF, surface-active substance) | 1.40 |
| Na phosphate buffer pH 7.0 | 1.10 |
| Na saccharinate | 0.10 |
| Flavour | 0.15 |
| Chlorhexidine digluconate | 0.2 |
| Sorbic acid | 0.20 |
| Hydrolite ® 5 | 0.15 |
| Vanillyl butyl ether | 0.15 |
| Dist. water | to 100 |

TABLE 35

Sugar-free chewing-gum (Amounts in % b.w.)

| Ingredients | Amount |
|---|---|
| Chewing gum base | 30.00 |
| Sorbitol. powder | Ad 100 |
| Palatinite | 9.50 |
| Xylitol | 2.00 |
| Mannitol | 3.00 |
| Aspartame | 0.10 |
| Acesulfame K | 0.10 |
| Emulgum/emulsifier | 0.30 |
| Sorbitol 70 %. in water | 14.00 |
| Glycerol | 1.00 |
| Flavor | 1.50 |
| Hydrolite ® 5 | 0.10 |
| Vanillyl butyl ether | 0.10 |

The invention claimed is:

1. A cosmetic blend, comprising
   (a) at least one TRPV1 and/or TRPV3 modulator representing a vanillyl ether according to formula (II)

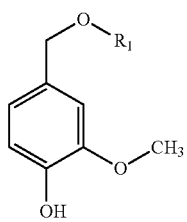

wherein $R_1$ stands for hydrogen or a C1-C7 alkyl radical, and
   (b) at least one 1,2-alkandiol selected from the group consisting of 1,2-pentandiol, 1,2-hexandiol, 1,2-heptandiol, 1,2-octandiol, 1,2-nonandiol, decandiol, 1,2-undecandiol, 1,2-dodecandiol, and mixtures thereof, and, optionally
   (c) at least one polyol having 3 to 12 carbon atoms and 3 to 6 hydroxyl groups.

2. The blend of claim 1, wherein said polyol is selected from the group consisting of glycerol, 1,2,ω-C4-C12-alkantriols obtained from reaction products of 1,2-epoxy-ω-hydroxyalkanes with water, oligoglycerol mixtures with a degree of self-condensation of 1.5 to 10, trimethylol ethane, trimethylol propane, trimethylol butane, pentaerythritol, dipentaerythritol, lower alkyl glucosides, sugar alcohols containing 5 to 12 carbon atoms, and mixtures thereof.

3. The blend of claim 1, wherein said components (a) and (b) are present in a ratio by weight of from about 10:90 to about 90:10.

4. The blend of claim 3, wherein said components (a) and (b) are present in a ratio by weight of from about 40:60 to 60:40.

5. A cosmetic or dermatological composition comprising the blend of claim 1 in an amount suitable to effect warming sensation on human skin or mucous membranes.

6. The composition of claim 5, comprising the blend in an amount of from 0.01 to about 5% by weight—calculated on the final composition.

7. The blend of claim 1, comprising
   (a) at least one TRPV1 and/or TRPV3 modulator representing the vanillyl ether according to formula (III)

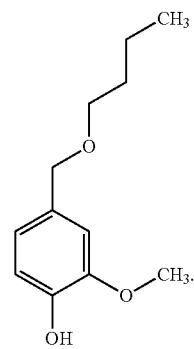

8. The blend of claim 1, wherein
   (b) the 1,2-alkandiol is selected from the group consisting of 1,2-hexandiol, 1,2-heptandiol, 1,2-octandiol, 1,2-nonandiol, 1,2-decandiol, 1,2-undecandiol, 1,2-dodecandiol, and mixtures thereof.

9. The blend of claim 8, wherein said 1,2-alkandiol is selected from the group consisting of 1,2-hexandiol, 1,2-octandiol and mixtures thereof.

10. A cosmetic bend, comprising
   (a) a TRPV1 and/or TRPV3 modulator which is vanillyl butyl ether, and
   (b) an 1,2-alkandiol selected from the group consisting of 1,2-hexandiol, 1,2-octandiol and mixtures thereof, and, optionally
   (c) at least one polyol having 3 to 12 carbon atoms and 3 to 6 hydroxyl groups.

* * * * *